(12) United States Patent  (10) Patent No.: US 9,055,956 B2
McRae et al.  (45) Date of Patent: Jun. 16, 2015

(54) METHODS AND APPARATUS FOR INTRODUCING TUMESCENT FLUID TO BODY TISSUE

(71) Applicant: Covidien LP, Mansfield, MA (US)

(72) Inventors: Robert Gordon McRae, San Jose, CA (US); Michael S. Mirizzi, San Jose, CA (US); Brady D. Esch, San Jose, CA (US); Anna Grace Prestezog, Sunnyvale, CA (US); Todd Schoenberger, Palo Alto, CA (US); Halil Ibrahim Karabey, San Jose, CA (US); Jeff Zalewski, Palo Alto, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/914,113

(22) Filed: Jun. 10, 2013

(65) Prior Publication Data

US 2014/0155879 A1    Jun. 5, 2014

Related U.S. Application Data

(63) Continuation of application No. 11/472,793, filed on Jun. 22, 2006, now Pat. No. 8,465,451.

(60) Provisional application No. 60/701,538, filed on Jul. 20, 2005, provisional application No. 60/693,366, filed on Jun. 22, 2005.

(51) Int. Cl.
*A61N 1/30* (2006.01)
*A61B 18/18* (2006.01)
(Continued)

(52) U.S. Cl.
CPC ............. *A61B 18/18* (2013.01); *A61B 18/1477* (2013.01); *A61B 18/1492* (2013.01); *A61B 2018/0016* (2013.01); *A61B 2018/00214* (2013.01); *A61B 2018/00404* (2013.01); *A61B 2018/1425* (2013.01); *A61B 2018/1475* (2013.01); *A61B 2218/002* (2013.01); *A61M 25/0068* (2013.01);
(Continued)

(58) Field of Classification Search
USPC .......................... 604/93.01, 508, 20; 606/32
See application file for complete search history.

(56) References Cited

U.S. PATENT DOCUMENTS 4,578,061 A    3/1986 Lemelson
5,336,178 A    8/1994 Kaplan et al.
(Continued)

FOREIGN PATENT DOCUMENTS

EP     1 350 481 A2    8/2003
WO     WO 03/049631 A1    6/2003

OTHER PUBLICATIONS

Bone Salat, "Endoluminal Diode-Laser Treatment of Varicose Veins, Preliminary Study," Patologia Vascular, Jan. 1999, 32-39, Spain.
Bone Salat, "Thesis, Master's Degree on Esthetic Medicine," University of the Balearic Islands, Palma De Mallorca, Oct. 1998.
Cohn et al., "Ambulatory Phlebectomy Using the Tumescent Technique for Local Anesthesia," Dermatol Surg 1995; 21:315-318, Elsevier Science.
(Continued)

*Primary Examiner* — Kevin C Sirmons
*Assistant Examiner* — Deanna K Hall
(74) *Attorney, Agent, or Firm* — Thomas M. Johnston, Esq.

(57) ABSTRACT

A catheter is usable to treat a hollow anatomical structure (HAS). The catheter comprises one or more shafts which extend away from a proximal end of the catheter toward a distal end thereof. The catheter further comprises an HAS constriction energy source located at or near the distal end of the catheter. The catheter further comprises at least one radially expandable transmural fluid delivery channel located in the catheter near the HAS constriction energy source.

17 Claims, 17 Drawing Sheets

(51) Int. Cl.
*A61M 25/00* (2006.01)
*A61B 18/14* (2006.01)
*A61B 18/00* (2006.01)

(52) U.S. Cl.
CPC ....... *A61M 25/0074* (2013.01); *A61M 25/0082* (2013.01); *A61M 25/0084* (2013.01); *A61M 2025/0087* (2013.01)

(56) References Cited

U.S. PATENT DOCUMENTS

| | | | |
|---|---|---|---|
| 5,354,279 | A | 10/1994 | Hofling |
| 5,364,356 | A | 11/1994 | Hofling |
| 5,419,777 | A | 5/1995 | Hofling |
| 5,464,395 | A | 11/1995 | Faxon |
| 5,538,504 | A | 7/1996 | Linden |
| 5,611,778 | A | 3/1997 | Brinou |
| 5,681,281 | A | 10/1997 | Vigil et al. |
| 5,693,029 | A | 12/1997 | Leonhardt |
| 5,713,863 | A | 2/1998 | Vigil et al. |
| 5,746,716 | A | 5/1998 | Vigil et al. |
| 5,830,222 | A | 11/1998 | Makower |
| 5,916,583 | A | 6/1999 | Broberg et al. |
| 6,102,904 | A | 8/2000 | Vigil et al. |
| 6,210,392 | B1 | 4/2001 | Vigil et al. |
| 6,217,554 | B1 | 4/2001 | Green |
| 6,258,084 | B1 | 7/2001 | Goldman et al. |
| 6,283,947 | B1 | 9/2001 | Mirzaee |
| 6,283,951 | B1 | 9/2001 | Flaherty et al. |
| 6,302,870 | B1 | 10/2001 | Jacobsen et al. |
| 6,309,375 | B1 | 10/2001 | Glines et al. |
| 6,312,402 | B1 | 11/2001 | Hansmann |
| 6,429,228 | B1 | 8/2002 | Inagi et al. |
| 6,458,098 | B1 | 10/2002 | Kanesaka |
| 6,514,248 | B1 | 2/2003 | Eggers et al. |
| 6,547,767 | B1 | 4/2003 | Moein |
| 6,599,267 | B1 | 7/2003 | Ray et al. |
| 6,602,241 | B2 | 8/2003 | Makower et al. |
| 6,685,648 | B2 | 2/2004 | Flaherty et al. |
| 6,692,466 | B1 | 2/2004 | Chow et al. |
| 6,752,803 | B2 | 6/2004 | Goldman et al. |
| 6,769,433 | B2 | 8/2004 | Zikorus et al. |
| 6,770,070 | B1 * | 8/2004 | Balbierz ................... 606/41 |
| 6,860,867 | B2 | 3/2005 | Seward et al. |
| 6,969,388 | B2 | 11/2005 | Goldman et al. |
| 6,984,239 | B1 | 1/2006 | Drasler et al. |
| 7,127,284 | B2 | 10/2006 | Seward |
| 7,163,533 | B2 | 1/2007 | Hobbs et al. |
| 2001/0016739 | A1 | 8/2001 | Goldman et al. |
| 2001/0041888 | A1 | 11/2001 | Goldman et al. |
| 2002/0183740 | A1 | 12/2002 | Edwards et al. |
| 2003/0191460 | A1 | 10/2003 | Hobbs et al. |
| 2004/0186435 | A1 | 9/2004 | Seward |
| 2005/0245862 | A1 | 11/2005 | Seward et al. |
| 2006/0030849 | A1 | 2/2006 | Mirizzi et al. |
| 2006/0085054 | A1 | 4/2006 | Zikorus et al. |
| 2006/0106338 | A1 | 5/2006 | Chang |
| 2006/0293647 | A1 | 12/2006 | McRae et al. |

OTHER PUBLICATIONS

Goldman, "Section II: Goldman Method—Preparation and Dosage", Ambulatory Phlebectomy, 74-76.
Gonschior et al., "A New Catheter for Prolonged Local Drug Application," Coronary Artery Disease, Apr. 1995, pp. 329-334, vol. 6, No. 4.
Gonschior et al., "Comparison of Local Intravascular Drug-Delivery Catheter Systems," American Heart Journal, Dec. 1995, pp. 1174-1181, vol. 130, No. 8, Mosby-Year Book, Inc.
International Search Report for Application No. PCT-US2006-024329 (the PCT counterpart of the parent application) mailed Mar. 1, 2007.
Korolenko, "Morphological Changes in Tissues After Novocain Solutions are Injected into Them Under Pressure," Medical Affairs, 1958, 831-34, 8, State Medical Publishing House, Ukraine.
Kuhnl et al., "C-Type Natriuretic Peptide Inhibits Constrictive Remodeling Without Compromising Re-Endothelialization in Balloon-Dilated Renal Arteries," J Endovasc Ther 2005; 12:171-182, The International Society of Endovascular Specialists.
Ogawa et al., "Electrothrombosis as a Treatment of Cirsoid Angioma in the Face and Scalp and Varicosis of the Leg," No. 3, 310-11.
Peridot Corp., "Case Study—Multi-Prong Infusion Needle," 2005.
Petrovsky, "Local Anesthesia," Big Medical Encyclopedia, 1974, 534-36, vol. 1, Soviet Encyclopedia, Moscow.
Proebstle et al., "High Ligation and Stripping of the Long Saphenous Vein Using the Tumescent Technique for Local Anesthesia," Dermatol Surg 1998; 24:149-153.
Ricci et al., "Technique of Phlebectomy," Ambulatory Phlebectomy, 66-126.
Ricci et al., "Anesthetic—Section I: Ricci-Georgiev Method—Preparation and Dosage," Ambulatory Phlebectomy, 71-74.
Ruju et al., "Stripping of the Internal Saphenous Vein by 'Tumescent Technique' and Under Local Anesthesia," Giornale Italiano Di Chirurgia Vascolare, Mar. 1998, 5:43-9, Italy.
Sattler, "Outpatient Surgery for Varicose Veins Under Tumescent Local Anaesthesia," Department of Dermatology, Darmstadt, Germany.
Smith et al., "Tumescent Anesthesia in Ambulatory Phlebectomy," Dermatol Surg 1998; 24:453-456.
Weiss et al., "Phlebectomy," Vein Diagnosis and Treatment: A Comprehensive Approach, Chapter 22, pp. 197-210, McGraw-Hill Medical Publishing Division, 2001.
Welch, "History of Tumescent Anesthesia, Part 1: From American Surgical Textbooks of the 1920s and 1930s," Aesthetic Surgery Journal, Sep./Oct. 1998, 353-56.
U.S. Appl. No. 11/472,793, filed Jun. 22, 2006, Office Actions dated Oct. 20, 2009, Jan. 12, 2009, Jun. 25, 2007, Decision on Appeal dated Feb. 4, 2013, Notice of Allowance dated Feb. 15, 2013.

* cited by examiner

METHODS AND APPARATUS FOR INTRODUCING TUMESCENT FLUID TO BODY TISSUE

CROSS-REFERENCE TO RELATED APPLICATIONS

This application is a continuation of application Ser. No. 11/472,793, filed Jun. 22, 2006, titled METHODS AND APPARATUS FOR INTRODUCING TUMESCENT FLUID TO BODY TISSUE, which claims the benefit under 35 U.S.C. §119(e) of U.S. Provisional Application No. 60/693,366, filed Jun. 22, 2005, titled METHODS AND APPARATUS FOR INTRODUCING TUMESCENT FLUID TO BODY TISSUE; and of U.S. Provisional Application No. 60/701,538, filed Jul. 20, 2005, titled METHODS AND APPARATUS FOR INTRODUCING TUMESCENT FLUID TO BODY TISSUE, the entire contents of each of which are hereby incorporated by reference herein and made part of this specification.

BACKGROUND

1. Field of the Invention

Certain embodiments disclosed herein relate generally to a method and apparatus for delivering tumescent fluids to body tissue. The target body tissue may surround a hollow anatomical structure such as a vein. Certain disclosed embodiments also relate generally to a method and apparatus for applying energy to constrict and/or shrink a hollow anatomical structure such as a vein, and more particularly, a method and apparatus to conduct electrical current and/or heat to the wall of the hollow anatomical structure.

2. Description of the Related Art

In endoluminal treatments of hollow anatomical structures (HAS's) such as varicose veins, a tumescent fluid is often applied to the tissue near the target HAS to partially constrict the walls thereof and place them in firm apposition with a therapeutic device in the HAS lumen. The tumescent fluid is usually applied via a series of injections through the skin of the patient into the underlying tissue which surrounds the HAS.

SUMMARY

In certain embodiments, a catheter treats a hollow anatomical structure (HAS). The catheter further comprises one or more shafts which extend away from a proximal end of the catheter toward a distal end thereof. The catheter further comprises an HAS constriction energy source located at or near the distal end of the catheter. The catheter further comprises at least one radially expandable transmural fluid delivery channel located in the catheter near the HAS constriction energy source.

In certain embodiments, the constriction energy source of the catheter comprises an electrically resistive heating element. In one embodiment, the resistive heating element of the catheter comprises a resistive coil. In another embodiment, the resistive heating element is located on an outer surface of one of one or more shafts, and the outer surface includes at least one port through which at least one fluid delivery channel is extendable. In certain embodiments, the constriction energy source of the catheter comprises at least one electrode.

In certain embodiments, one or more catheter shafts comprises a first shaft which carries at least one electrode, and a second shaft which carries at least one fluid delivery channel. In certain embodiments, the first and second shafts are coaxial. In one embodiment, at least one electrode of the catheter comprises a plurality of electrodes. The first electrode is spaced longitudinally from a second electrode along an outer surface of one of one or more catheter shafts.

In certain embodiments, the fluid delivery channel comprises at least one needle. In one embodiment, the needle of the catheter has a sharp tip and a fluid delivery port at or near the tip. In one embodiment, the fluid delivery channel of the catheter comprises at least one perforating jet. In certain embodiments, the catheter further comprises source of tumescent fluid which is in fluid communication with the fluid delivery channel. In certain embodiments, one or more catheter shafts comprise a plurality of shafts which are arranged coaxially. In one embodiment, the first and second shafts are coaxial.

In certain embodiments, a catheter treats a hollow anatomical structure. The catheter further comprises a shaft which extends from a proximal end to a distal end thereof. The catheter further comprises a therapeutic energy source located at or near a distal end of the shaft. The therapeutic energy source comprises at least one of an electrode and a resistive heating element. At least one fluid delivery channel is located in the shaft. The channel has a delivery tip which is movable from a retracted position near a longitudinal axis of the shaft, to a deployed position farther from the longitudinal axis.

In certain embodiments, the therapeutic energy source comprises a plurality of electrodes. A first electrode is spaced longitudinally along the catheter from a second electrode. In one embodiment, the fluid delivery channel comprises at least one needle. In another embodiment, the needle has a sharp tip and a fluid delivery port at or near the tip. In certain embodiments, the fluid delivery channel comprises at least one perforating jet. In certain embodiments, the catheter further comprises a source of tumescent fluid which is in fluid communication with the fluid delivery channel.

In certain embodiments, a method treats a hollow anatomical structure with a catheter having one or more shafts which extend away from a proximal end of the catheter toward a distal end thereof. The method further comprises conducting a fluid, via a fluid delivery channel of the catheter, from a location within the hollow anatomical structure and within one of the shafts, to a tip of the channel which is located radially outward from one or more shafts. A therapeutic energy source of the catheter system passes energy into a wall of the hollow anatomical structure. The energy constricts the hollow anatomical structure.

In certain embodiments, passing energy comprises driving RF energy through the wall of the hollow anatomical structure with at least one electrode of the catheter. In one embodiment, passing energy comprises heating the wall of the hollow anatomical structure with at least one heating element of the catheter system. In another embodiment, conducting the fluid comprises conducting the fluid through the wall of the hollow anatomical structure. In certain embodiments, the method further comprises penetrating the wall of the hollow anatomical structure with the channel.

In certain embodiments, conducting the fluid comprises conducting tumescent fluid into tissue near the hollow anatomical structure and thereby initially constricting the hollow anatomical structure. In one embodiment, passing energy comprises passing energy after the initial constriction of the hollow anatomical structure. In another embodiments, after passing the energy, the method further comprises moving the energy source along the hollow anatomical structure to a first subsequent treatment position, and conducting the fluid via the fluid delivery channel into tissue adjacent the hollow anatomical structure near the first subsequent treatment position. In certain embodiments, the method further comprises passing the energy while the energy source is at the first subsequent treatment position.

In certain embodiments, a catheter treats a hollow anatomical structure. The catheter further comprises a shaft which extends from a proximal end to a distal end thereof. The catheter further comprises a therapeutic energy source located at or near a distal end of the shaft. The therapeutic energy source forms an energy coupling surface which faces generally radially outward from the shaft. At least one fluid delivery channel extends in a generally radial direction through at least one of the energy source and a sidewall of the shaft. The fluid delivery channel has an outer endpoint positioned in a locally radially outermost region of the energy source or the shaft.

In certain embodiments, the energy coupling surface of the catheter is fixed relative to the shaft. In one embodiment, the fluid delivery channel extends through the energy source. In another embodiment, the energy source of the catheter is an electrode. In certain embodiments, the energy source is a heat emitting element. In one embodiment, the heat emitting element is an electrically resistive heater. In another embodiment, the heat emitting element is a heating coil. In certain embodiments, the fluid delivery channel extends through the heating coil.

Certain objects and advantages of the disclosed invention(s) are described herein. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The embodiments summarized above are intended to be within the scope of the invention(s) herein disclosed. However, despite the foregoing discussion of certain embodiments, only the appended claims (and not the present summary) are intended to define the invention(s). The summarized embodiments, and other embodiments of the present invention, will become readily apparent to those skilled in the art from the following detailed description of the preferred embodiments having reference to the attached figures, the invention(s) not being limited to any particular embodiment(s) disclosed.

DETAILED DESCRIPTION OF THE PREFERRED EMBODIMENTS

Figure 1:
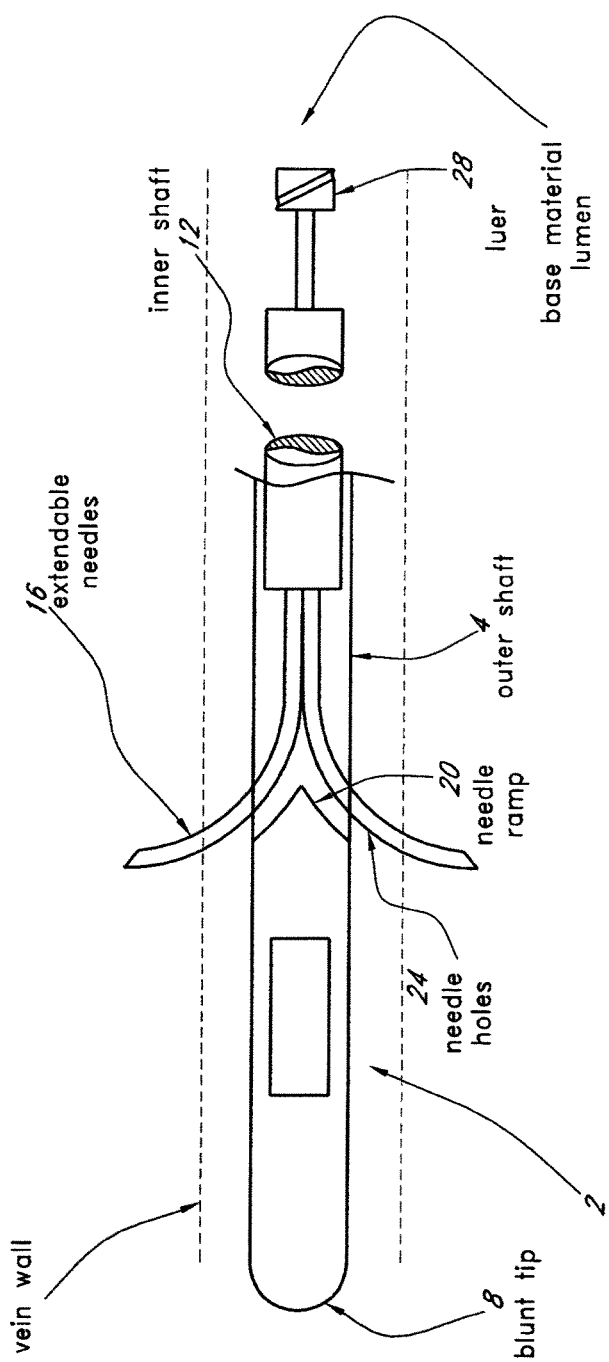
FIG. 1 is a view of one embodiment of a device that delivers tumescent fluid with needles.

The features of the system and method will now be described with reference to the drawings summarized above. The drawings, associated descriptions, and specific implementation are provided to illustrate embodiments of the invention(s) and not to limit the scope of the invention(s).

In addition, methods and functions described herein are not limited to any particular sequence, and the acts or states relating thereto can be performed in other sequences that are appropriate. For example, described acts or states may be performed in an order other than that specifically disclosed, or multiple acts or states may be combined in a single act or state.

In some embodiments, a fluid is introduced into body tissue surrounding a vein or other hollow anatomical structure (HAS) to act as a bulking agent around the HAS, causing a localized diameter reduction. The target body tissue may surround a HAS such as a fallopian tube or vas deferens, artery, and vein including but not limited to superficial and perforator veins, hemorrhoids, esophageal varices, ovarian veins, and varicoceles. Preferably, the fluid is introduced to the fascial envelope, which is the area surrounding a vessel. Preferably, tumescent anesthesia is the fluid that is introduced. Preferably, over a short period of time, tissue in growth would fill the bulk space, providing a fibrotic "scaffolding" around the vessel. This diameter reduction at or near a valve could promote valve competency restoration.

In some embodiments, the tumescent fluid may be introduced into body tissue from within the HAS and through the walls of a HAS. In other embodiments, the tumescent fluid is introduced from outside the HAS. Some embodiments combine the introduction of tumescent fluids with therapeutic features, such as heating coil therapy or RF Electrode therapy. Some embodiments relate to a method for compressing an anatomical structure prior to or during the application of energy and an apparatus including an electrode device having multiple leads for applying energy to the compressed structure to cause it to durably assume its compressed form.

Some embodiments are directed to a method and apparatus for applying energy to a hollow anatomical structure such as a vein, to shrink the structure. More detailed aspects of these embodiments are directed to pre-compressing and exsanguinating a hollow anatomical structure while providing anesthetic and insulation benefits during a procedure of shrinking the hollow anatomical structure.

In another aspect, a method comprises providing fluid to tissue surrounding a hollow anatomical structure to induce tumescence of the tissue and consequent compression of the hollow anatomical structure during a procedure of applying energy to the hollow anatomical structure from within the structure. In a more detailed aspect, the method comprises introducing into the hollow anatomical structure a catheter having a working end and at least one electrode at the working end, placing the electrode into contact with the inner wall of the pre-compressed hollow anatomical structure, and applying energy to the hollow anatomical structure at the treatment site via the electrode until the hollow anatomical structure durably assumes dimensions less than or equal to the pre-compressed dimensions caused by the injection of the solution into the tissue.

In another aspect, a method comprises providing fluid to tissue surrounding a hollow anatomical structure to induce tumescence of the tissue and consequent compression of the hollow anatomical structure during a procedure of applying energy to the hollow anatomical structure from within the structure. In a more detailed aspect, the method comprises introducing into the hollow anatomical structure a catheter having a working end and at least one electrode at the working end, placing the electrode into contact with the inner wall of the pre-compressed hollow anatomical structure, and applying energy to the hollow anatomical structure at the treatment site via the electrode until the hollow anatomical structure durably assumes dimensions less than or equal to the pre-compressed dimensions caused by the injection of the solution into the tissue.

In a more detailed aspect, tumescent anesthesia fluid is injected or otherwise provided to tissue contiguous with a vein to compress the vein to about a desired final diameter. A catheter having an energy application device, such as expandable electrodes, is introduced internal to the vein at a site within the compressed portion of the vein and energy is applied to the internal vein wall by the application device. Sufficient energy is applied to cause the vein to durably assume the compressed diameter such that when the effects of the tumescent anesthesia fluid are dissipated, the vein retains the compressed diameter.

In some embodiments, the following method is used: (1) Place the device in the desired location; (2) inject or otherwise introduce tumescent fluid; (3) turn on the therapeutic energy source (RF, Heating Coil, or other). In some embodiments, the tumescent fluid is injected by needles or by high pressure fluid. In other embodiments, the fluid is released and allowed to disperse or mechanically dispersed to the targeted body tissue.

I. Endovascular/Endoluminal Tumescent Fluid Delivery Systems

Some embodiments comprise a device and method for introducing tumescent fluid into body tissue surrounding a HAS. One possible method for introducing the tumescent fluid is from within the HAS lumen and through the walls of a HAS. Preferably, a catheter is used to insert the device into or through the HAS, and the catheter includes a lumen to position the catheter within the HAS. In some embodiments, the shape of the catheter lumen is triangular, square, oval, semi-circular or a multi-lumen design to facilitate alignment. In some embodiments the device includes needles to inject the tumescent fluid through the vessel walls. In other embodiments, the tumescent fluid penetrates the vessel walls by way of pressurized fluid flow.

In some embodiments, the endovascular approach includes the following steps: (1) Use a compression means and Doppler Ultrasound to identify the location of the target valve; (2) compress the target region and assess whether the reduced diameter does indeed rectify the incompetence; (3) mark the location on the skin; (4) obtain HAS access via a sheath or other suitable means; (5) lay the delivery catheter down onto the skin and mark the distance between the access point and tip using the target valve position mark on the skin; (6) introduce the catheter into the vessel and position at the target location; (7) deploy extendable needles through the HAS (for embodiments using needles); (8) flush the lumen with the base material until a sufficient volume tumesces the area surrounding the HAS; (9) retract the needles (for appropriate embodiments) and withdraw the catheter; (10) perform a post-op scan to assess valve competence.

A. Needles for Introducing Tumescent Fluid

One embodiment involves a method and device for delivering tumescent fluid to body tissue by using needles to penetrate through a HAS wall. The needles may be flexible and contained within a channel in the catheter that is separate from a channel containing a lumen. The flexible needles could be pushed through this channel to penetrate the HAS wall. Alternatively, the needles may be retained in a sliding outer sleeve and deployed by retracting the sleeve. It is also contemplated that needles are pushed distally to extend beyond the sleeve (opposed to retraction of sleeve). In some embodiments, the needles are extended and retracted by mechanical means. For example, a threaded hub located near the proximal end of the device could mate with a threaded luer that is attached to the needles, and rotation of the luer could extend and retract the needles.

There may be any number of needles, and the needles may have any suitable shape or orientation. For example, the needles could be flexible, and several could be placed around the perimeter of the device so as to introduce tumescent fluid to multiple locations around the perimeter of the HAS. Multiple needles may also be oriented radially at the distal tip of the device. Additionally, it is contemplated that the needles are in multiple locations along the length of the device to introduce tumescent fluid along a length of the HAS. In some embodiments, the shape of the needle could be straight when cooled and curved outward when heated. The temperature of the human body may provide the heat to induce the curve in the needle, and cold tumescent fluid could be introduced to return the needle to its cold shape (i.e. Shape-Memory NiTi). In some embodiments, the shape of the needle could be predetermined and set so that at body temperature the curve in the needle is always present when not under load (i.e. Superelastic NiTi). In another embodiment, the needle is configured to telescope, and hydraulic pressure extends the telescoping needle.

Preferably, as shown in FIG. 1 needles 16 are introduced to the interior of the HAS by way of a catheter 2. Additionally, in some embodiments, a lumen is used to introduce and position the needles in the HAS. In some embodiments, impedance is used to sense the location of the needle tip. Preferably, the catheter 2 is configured with an outer shaft 4, tip 8, inner shaft 12, needles 16, needle ramp 20, needle holes 24, and a luer 28. In some embodiments, the outer shaft 4 is tubular, and the inner shaft 12, needles 16, and needle ramp 20 are located within the outer shaft 4. The tip 8 may be located at the distal end of the outer shaft 4, and the distal end of the tip 8 may be rounded for HAS trackability. The tip 8 may be sized such that its outer diameter is roughly equal to the outer diameter of the outer shaft 4. The luer 28 may be connected to the proximal end of the inner shaft 12, and the luer 28 and inner shaft 12 may be moveable with respect to the outer shaft 4. The needles 16 may be connected at their proximal end to the distal end of the inner shaft 12.

In some embodiments, the needles 16, when retracted, extend longitudinally from the distal end of the inner shaft 12 and are beveled and sharp at their distal end, which is the preferable end to penetrate the body tissue. Preferably, the needles 16 are steel and configured to extend in the radial direction when they contact the needle ramp 20 and spring back to their longitudinal position when retracted. In other embodiments, the needles 16 may also be preformed to bend radially outward prior to being extended. Additionally, the needles 16 could be made from nickel titanium and have a preformed shape that bends radially outward when heated. At lower temperatures, the needles 16 may extend longitudinally, and the heat of the human body may cause them to take on their preformed shape (making use of the material's shape-memory properties). The needles 16 may also have a preformed shape at all temperatures above a temperature lower than body temperature so that their shape is predetermined and shape change is effected by stress inducing martensite under load from their more stable austenitic form (making use of the material's superelastic properties). Preferably, the needle ramp 20 is fixed relative to the outer shaft 4 and is located distal from the inner shaft 12. The needle ramp 20 may be configured with a rounded or sloping surface(s) that angle towards the distal tip from the center of the outer shaft 4. The needle holes 24 may be located in the outer shaft 4 at a position proximal relative to where the needle ramp 20 is fixed to the outer shaft 4. In some embodiments, the needle holes 24 may be covered by a pierceable membrane, and the needles 16 may penetrate the membrane when extended. In some embodiments, the needles are configures for simultaneous deployment. Alternatively, the needles may be uncoupled and capable of independent deployment.

The catheter 2 may be inserted through the HAS until the needles 16 are positioned in a desired location. Preferably, the needles 16 are contained within the outer shaft 4 while the catheter 2 is being positioned within the HAS. In some embodiments, after the catheter 2 is in the desired location, the needles 16 extend through the needle holes 24 beyond the outside surface of the outer shaft 4 and into the body tissue surrounding the HAS. The catheter 2 may be configured such that a user can move the luer 28 to move the inner shaft 12 and needles 16 relative to the outer shaft 4 and needle ramp 20. In some embodiments, as the needles 16 move distal relative the needle ramp 20, the needles 16 contact and slide on the needle ramp 20 such that they bend outward and extend through the needle holes 24. Preferably, as the needles 16 are extended, they penetrate the HAS walls 32 and extend into the surrounding body tissue. Preferably, there is a pumping mechanism that sends the tumescent fluid through the inner shaft 12 to the needles 16, such that the fluid is injected into the body tissue after the needles 16 have penetrated the HAS walls 32. In some embodiments, the inner diameter of the needle and/or catheter is increased to accommodate pumped tumescent fluid.

Figure 1A:
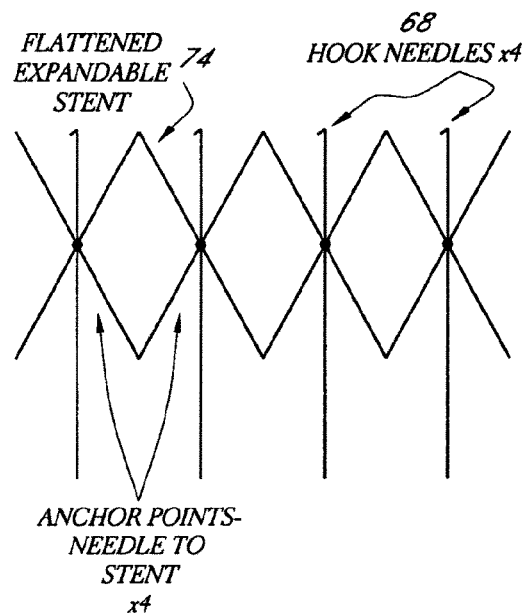
FIG. 1A is a top view of one embodiment of needles attached to an unrolled expandable stent.
Figure 1B:
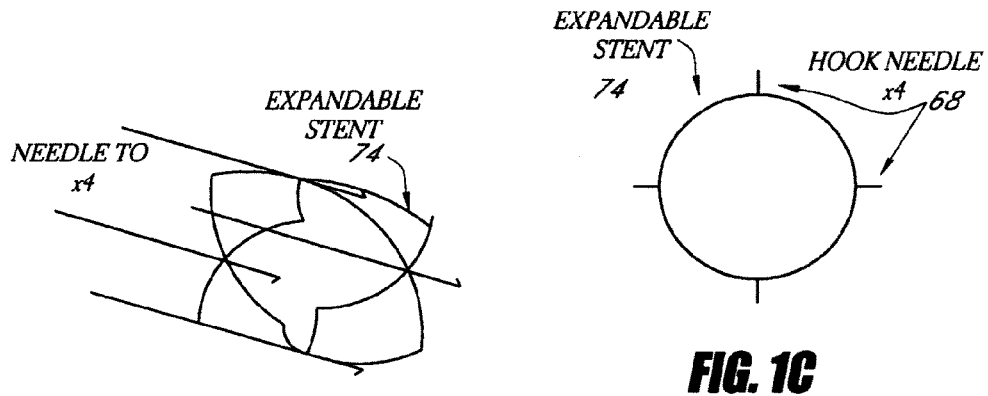
FIG. 1B is a perspective view of the needles and expandable stent of FIG. 1A when the stent is expanded.
Figure 1C:
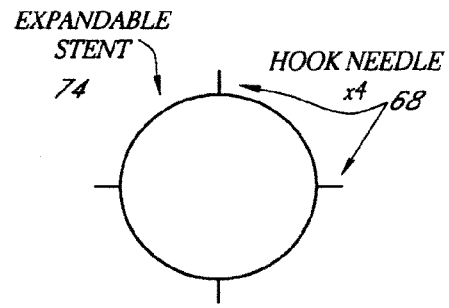
FIG. 1C is a cross-sectional view of the needles and expandable stent of FIG. 1B.

In some embodiments the tumescent fluid is delivered via hooked needles 68, as depicted in FIGS. 1A and 1B. The hooked needles 68 may be shaped such that their distal ends point at least partially in the proximal direction. Alternatively, in some embodiments the needles may be straight and are not hooked. In some embodiments, the hooked needles 68 are attached to an expandable stent 74 that is located at or near the proximal end of a catheter or other delivery device. In other embodiments, the stent 74 may be at other locations relative to the catheter. In some embodiments, the stent 74 is non-expanded when it is introduced through the HAS. Preferably, when the hooked needles 68 are in the desired location, the expandable stent 74 is expanded to push the hooked needles 68 out against the HAS wall. The shape of stent-needle construct 74 and 68 together may be such that the needles exit the delivery device at a smaller diameter and the perimeter increases from its proximal to distal end. In some embodiments, the stent 74 is expanded and collapsed by mechanical means such as opposing push/pull wires. In other embodiments, the stent 74 may be expanded by use of a silicone balloon. In other embodiments, the stent 74 may expand and collapse by using the shape-memory or superelastic properties of Shape Memory Alloys such as nickel titanium. Preferably, after the stent 74 is expanded and the hook needles 68 are positioned against the HAS wall, they are pulled back and the hooked needles 68 will penetrate the HAS walls. Preferably, tumescent fluid is injected into the surrounding tissue via the hooked needles 68 after the hooked needles 68 penetrate the HAS walls. In some embodiments, there is a common delivery fluid tube that delivers fluid to all of the hooked needles 68, which may extend through the interior of the catheter. Alternatively, fluid can be independently delivered to each needle allowing for independent control of fluid delivery. Preferably, after the tumescent fluid is injected in the surrounding tissue, the expandable stent 74 is collapsed to retract the hooked needles 68. In some embodiments, this process is repeated several times to inject tumescent fluid over a desired length of the HAS. Preferably, there are four hooked needles 68 equally spaced along the perimeter of the expandable stent 74, but there can be any number of hooked needles 68. There can also be multiple rows of hooked needles 68 attached along the length of the expandable stent 74.

In some embodiments, the device includes a manifold at the proximal hub that allows one or more of the needles to be turned off or on to fluid delivery or aspiration. One advantage of this is that tumescent fluid could be introduced in specific locations relative to the HAS, which allows for infiltration above a HAS to push it down away from the skin. Additionally, this will allow selective treatment of body tissue and prevent non-targeted body tissue (i.e. other vessels including veins and arteries) from being treated. In a further embodiment, the device may not include a manifold and each needle or set of needles are independently injected and aspirated.

Some embodiments include features for determining the directional orientation of the needle(s) to allow a user to know which needle is directed anteriorly non-targeted body tissue is not infiltrated. For example, there could be a shaft marker located on the shaft to indicate the orientation of the needle(s) which indicates which way is anterior. Alternatively, there can be a method in which a test infiltration is performed to observe or visualize where the injection occurred around the vessel. Furthermore, a method may include an aspirating step before injecting tumescent to make sure the needle is outside the vessel (i.e. blood flashback may indicate that the needle is not outside the vessel).

In some embodiments, features are included to ensure that needles are penetrating the HAS wall and are not in the blood stream, which may be especially relevant when treating large vessels. In one embodiment, the stroke length of each needle deployment is independently controlled in an uncoupled construct, and in another embodiment the stroke length is simultaneously controlled in a coupled construct. Advantageously, when treating large vessels this may help to ensure that a single needle doesn't remain in the blood stream. This stroke length could range anywhere from about 0.3 cm to 2 cm and is preferably about 0.5 cm to 1 cm. In an alternative embodiment, the needles may be aspirated, one at a time, before injecting tumescent to make sure the needles are outside the HAS wall (i.e. blood flashback would indicate the needle is not outside the HAS). In a further embodiment, a balloon is inflated on the shaft near the location where the needle exits to center the shaft in the center of the vessel so that the needles all equally penetrate the HAS wall when deployed. Another embodiment may apply a vacuum force to pull a HAS down to the shaft before deploying the needles.

In some embodiments, the depth of penetration of the needles is limited. For example, stopping features (i.e. raised feature, swaged needle shaft itself, polymer flap, etc.) on the needle shaft proximal to the piercing tip may limit how far the needle can penetrate the vessel wall. It is also contemplated that the stopping feature could be distal the piercing tip (i.e., for hooked needles). In addition, embodiments that combine this feature with independent control of deployment or needle stroke length would allow a user to center the catheter in the HAS by mechanically biasing the catheter away from one side of the HAS. Preferably, once the stopping feature engages the vessel wall any further deployment of the needle would push the catheter assembly toward the center of the lumen (i.e. self centering), which improves the likelihood that all needles pierce through the vessel wall. Preferably, the stopping features are far enough back from the tip of the needle(s) to allow the sharp tip of the needle to penetrate all the way through the vessel wall, but not so far as would damage other structures in the area or pierce through the skin. For example the distance between the tip of the needle and the stopper is preferably about 0.3 cm to 1 cm, more preferably between about 0.3 cm and 0.6 cm.

In further embodiments, a Piezo electric crystal can be mechanically coupled to the needle(s) to vibrate them to allow for ease of HAS wall cutting and penetration.

B. Pressurized Fluid Delivery

Figure 2:
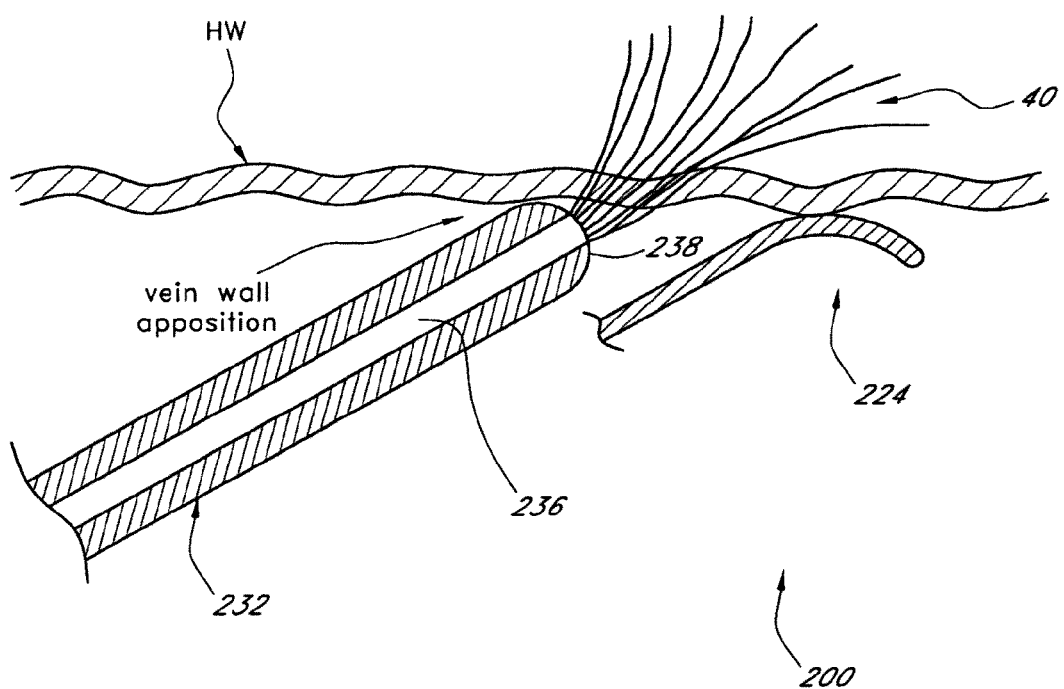
FIG. 2 is a partial side view of one embodiment of a device that delivers pressurized tumescent fluid.

In another embodiment as seen in FIG. 2, the tumescent fluid is delivered through the HAS wall HW by way of pressurized fluid 40. In one embodiment, a micro-perforating jet 232 is positioned against or near the HAS wall HW and pressurized fluid 40 is pumped through the micro-perforating jet 232 such that it contacts and penetrates the HAS wall HW and enters the surrounding tissue. FIG. 2 also depicts an electrode 224, which can be used for therapeutic purposes and is described in more detail below.

Figure 3:
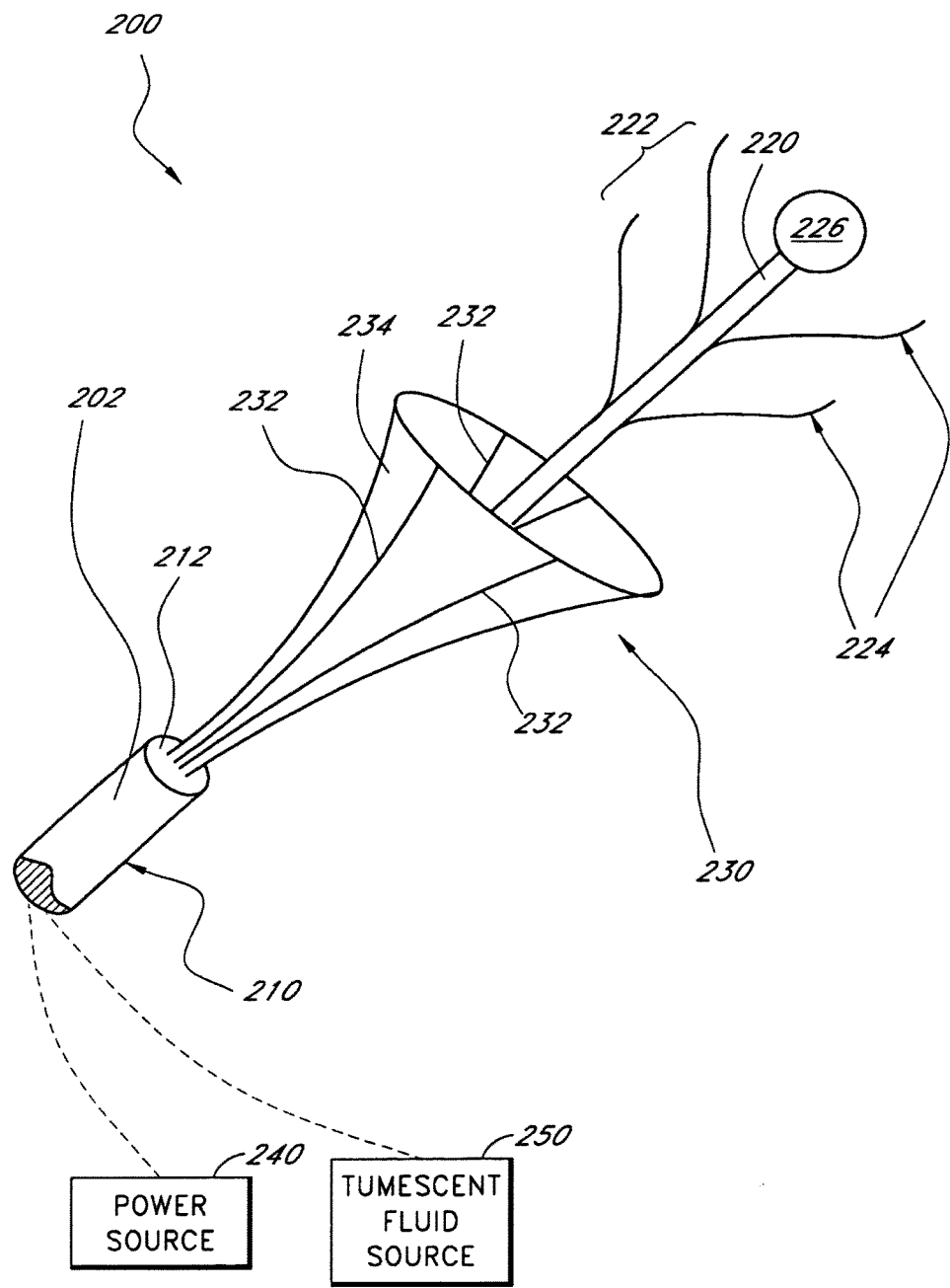
FIG. 3 is a perspective view of another embodiment of a device that delivers pressurized tumescent fluid.
Figure 4:
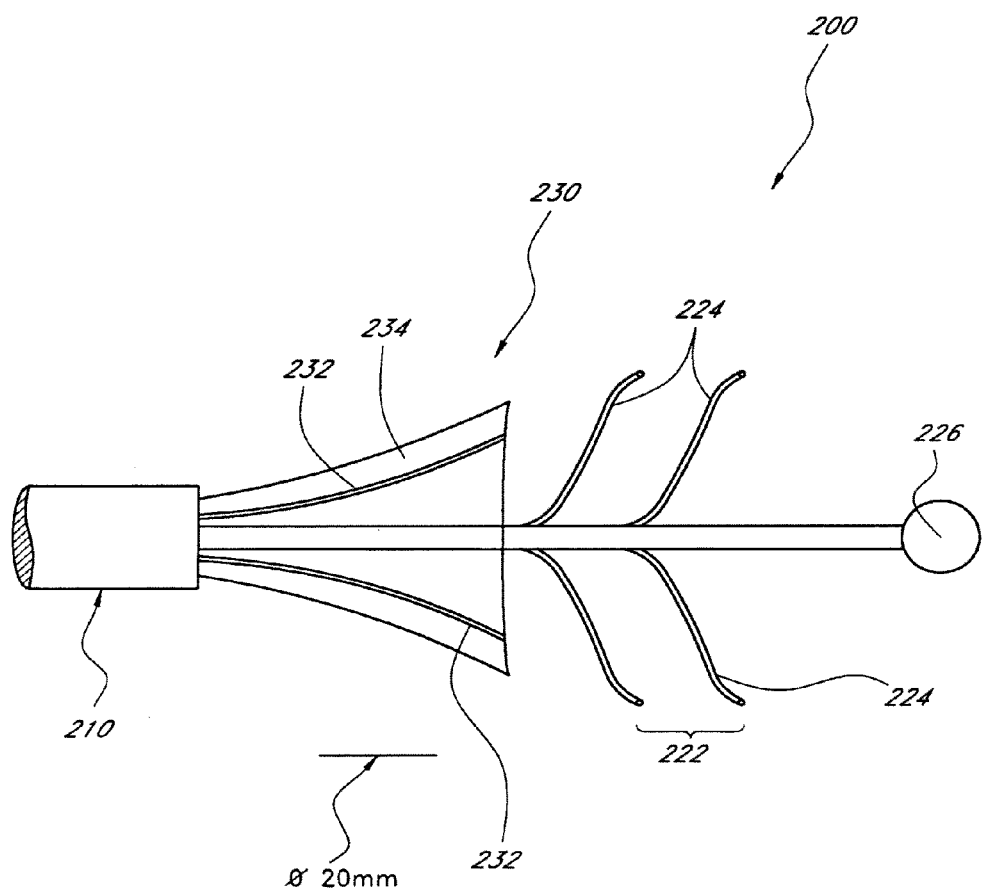
FIG. 4 is a side view of the tumescent fluid delivery device of FIG. 3.

In further embodiments, the structure that delivers the pressurized fluid may be shaped so as to locate and orient the jet 232 and pressurized fluid 40 in a desired position relative to the HAS wall HW. For example, as shown in FIGS. 3 and 4, the pressurized fluid 40 may be delivered through fluid channel ribs 232 that extend along a catheter 200. Preferably, the fluid channel ribs 232 are extendible beyond the distal end of the catheter outer shaft 210. In the portions that extend beyond the distal end of the outer shaft 210, the fluid channel ribs 232 may be located within an umbrella exsanguinator 230. The shape of the umbrella exsanguinator 230 may be such that the perimeter increases from its proximal to distal end. Preferably, the umbrella exsanguinator 230 is sized to position the distal end of the fluid channel ribs 232 against or near the HAS wall. There may be several fluid channel ribs 232 located within the umbrella exsanguinator 230, which will allow the pressurized fluid 40 to contact and penetrate the HAS wall in multiple locations.

Figure 5:
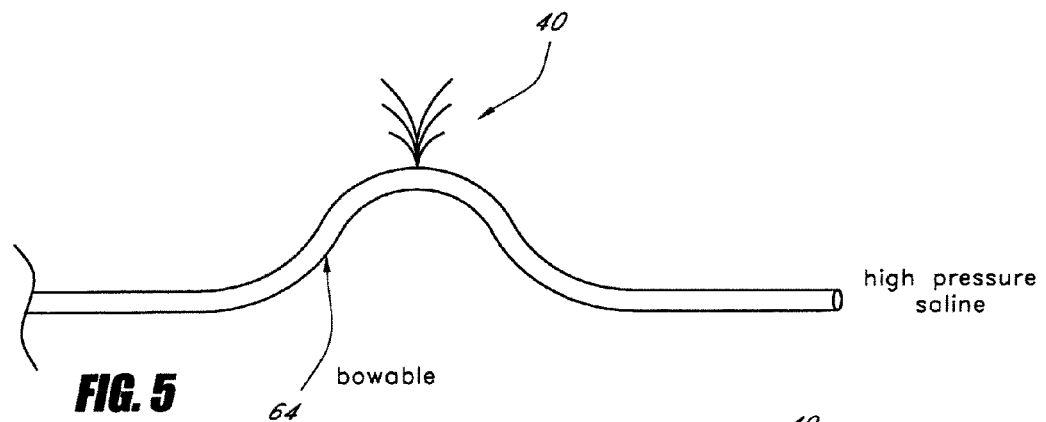
FIG. 5 is a perspective view of one embodiment of a device configured to deliver pressurized tumescent fluids.
Figure 6:
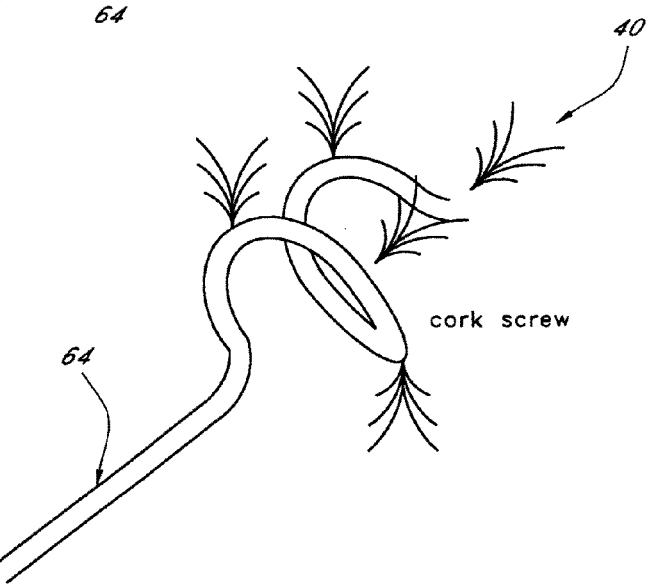
FIG. 6 is another embodiment of a device configured to deliver pressurized tumescent fluids.

In further embodiments as shown in FIG. 5, the high pressure fluid 40 may be delivered through a delivery tube 64 that is shaped such that the pressurized tumescent fluid exits the delivery tube 64 in a desired direction and at a desired location relative to the HAS wall 32. In some configurations, this is accomplished with a bowable fluid delivery tube 64 that is curved as shown in FIG. 5. In other embodiments, the fluid delivery tube 64 is corkscrew shaped as shown in FIG. 6. This allows multiple exits of the pressurized fluid 40, all of which can be positioned at or near the HAS wall, which allows pressurized fluid 40 to penetrate the HAS wall in multiple locations.

Preferably, the fluid delivery tubes 64 are made of nickel titanium and are formed such that they are straight at a lower temperature and transition into a pre-formed shape when heated (making use of the material's shape-memory properties). In this manner, the fluid delivery tubes 64 can be inserted within the vein in a roughly straight shape and can take on the desired shape as the temperature is increased to that of the human body. Alternatively, the tubes 64 can exist pre-formed at temperatures of use well below body temperature such that they transition to a straight shape by stress-inducing a martensitic phase change in the material while being delivered (making use of the material's superelastic properties). However, the fluid delivery tubes 64 can be formed according to any known manufacturing methods.

II. Endoluminal Tumescent Fluid Delivery Combined with Vein Therapy

Some embodiments combine delivery of tumescent fluids with HAS therapy. The therapy may consist of coagulating and/or constricting a HAS in order to inhibit or stop fluid flow therethrough. By "constricting," it is meant that a portion of the lumen of the treated HAS is reduced in size so that fluid flow therethrough is either reduced or stopped entirely. Usually, constriction will result from endothelial denudation, a combination of edema and swelling associated with cellular thermal injury, and denaturation and contraction of the collagenous tissues leading to a fibrotic occlusion of the HAS so that fluid flow is reduced or stopped entirely. In other cases, constriction could result from direct fusion or welding of the walls together, typically when pressure and/or energy are applied externally to the HAS. Such heating may occur as a result of the application of energy directly to the walls of the HAS and/or to the tissue surrounding the HAS. Preferably, this energy is provided consistent with known therapies, such as RF electrode therapy, heating coil therapy, or perforator vein therapy. In some embodiments, the therapy includes the following steps: (1) Place the device in the desired location; (2) extend the needle(s) through the HAS wall (for needle embodiments); (3) inject tumescent fluid; (4) turn on the therapeutic energy source (RF, Coil, or other); (5) move the device axially/longitudinally within the HAS to a new, adjacent treatment location and repeat steps 2 through 4. In some embodiments, tumescent fluid is introduced into a section surrounding the HAS while therapy is being provided to another section. This allows two actions to be conducted simultaneously, which may increase the efficiency of the treatment. It is contemplated that all embodiments of introducing tumescent fluid to body tissue can be combined with HAS therapy techniques. However, in some embodiments, the two actions may not be conducted simultaneously because the time necessary for the tumescent fluid to be injected and to take effect can require a longer duration than the time necessary for the therapeutic energy source to take effect. For a more efficient and effective result, tumescent fluid can be administered with more than one needle.

A. RF Electrode Therapy Combined with Tumescent Fluid Delivery

In some embodiments, an HAS treatment device includes a catheter with electrodes, which can be used to provide RF therapy to a HAS. In some embodiments, the catheter may include an expandable electrode device that moves in and out of the distal end of the catheter's outer shaft 210. Preferably, the electrode device includes a plurality of electrodes 224 which can be expanded by moving the electrodes 224 within the shaft 210, or by moving the outer shaft 210 relative to the electrodes 224. RF Electrode Therapy devices and methods are described in more detail in U.S. Pat. No. 6,769,433, issued on Aug. 3, 2004 to Zikorus et. al., titled EXPANDABLE VEIN LIGATOR CATHETER HAVING MULTIPLE ELECTRODE LEADS, AND METHOD, which is hereby incorporated by reference herein and made a part of this specification.

1) Pressurized Tumescent Fluid Combined with RF Electrode Therapy

In some embodiments, RF electrode therapy is provided in combination with a tumescent fluid delivery system that delivers pressurized fluid through the HAS wall with a microperforating jet, as depicted in FIGS. 2-6. Preferably, one or more electrodes 224 are located on a treatment catheter distal of one or more micro-perforating jets 232, as depicted in FIG. 2, but it is contemplated that they could be positioned otherwise. The electrodes 224 may be positioned for delivery into the HAS within a surrounding or overlying structure that delivers the pressurized fluid 40. For example, as shown in FIGS. 3 and 4, the electrodes 224 may be folded within an umbrella exsanguinator 230 and outer shaft 210 during insertion into the HAS and then, after insertion, be moved distally relative to the umbrella 230 and outer shaft 210 to deploy the electrodes 224. Alternatively, the umbrella 230 and outer shaft 210 may be moved proximally relative to the electrodes 224.

FIGS. 2-4 show an HAS treatment catheter 200 which includes an electrode device having multiple electrodes for applying energy to shrink a hollow anatomical structure. This catheter can be used to treat varicose veins by way of ligation. Alternatively, this catheter can be used to treat varicose veins by collagen contraction and cellular necrosis of the vessel wall leading to ultimate fibrotic occlusion of the vessel lumen. This occlusion, cauterization, and/or coagulation of the vascular lumina can be accomplished using electrical energy applied through an electrode device. A treatment device such as the catheter 200 is introduced into the vein lumen and positioned so that it contacts the vein wall. Once the catheter is properly positioned, RF energy is applied to the vein wall through the electrode device thereby causing the vein wall to shrink in cross-sectional diameter. A reduction in cross-sectional diameter, for example from 5 mm (0.2 in) to 1 mm (0.04 in) or more often from larger diameters of 8-16 mm (0.35 in-0.63 in) in 1 mm (0.04 in), significantly reduces the flow of blood through the vein and results in an effective occlusion and/or ligation.

In some embodiments, the treatment catheter 200 is comprised of an outer catheter shaft 210, and an inner shaft 220 and surrounding umbrella exsanguinator 230 which are slidingly received within a lumen 212 of the outer shaft 210. The inner shaft 220 and umbrella 230 may be slidable together as a unit within the outer shaft lumen 212, or they may be separately and independently slidable. An HAS constriction energy source in the form of an electrode array 222 is mounted on the inner shaft 220, and includes one or more radially expandable electrodes 224. The inner shaft 220 preferably includes an atraumatic tip 226 at the distal end thereof, to minimize tissue injury as the catheter 200 is passed through a narrow HAS.

In additional embodiments, an HAS constriction energy source in the form of one or more heating elements is disposed on the inner shaft 220 or outer shaft 210, and preferably at or near a working end or distal end of the shaft 220/210. In one embodiment, the heating element comprises an electrically resistive coil, but in alternative embodiments any other suitable heat-emitting device may be employed, such as other electrically resistive heaters, a fluid-conducting heat exchanger, a chemical reaction chamber, etc. The heating element employed on the shaft 220/210 can be generally similar to the various embodiments of heating elements discussed elsewhere herein. Additionally, where a heating element is employed the proximal portion of the shaft 220/210 may include indexing marks as discussed elsewhere herein to facilitate "indexed" operation of the heating element to treat an HAS.

The umbrella 230 preferably includes one or more radially expandable transmural fluid delivery channels in the form of fluid channel ribs 232, and a membrane 234 which is supported by the fluid channel ribs 232. (The functions of the fluid channel ribs 232 and membrane 234 will be discussed in greater detail below.) In alternative embodiments of the catheter 200, the membrane 234 can be omitted such that the umbrella 230 includes only the fluid channel rib(s) 232. In still further embodiments, fewer than all of the ribs 232 include fluid channels therein; in other words, one or more of the ribs can be simple structural members without fluid conducting capabilities.

The catheter 200 can be manipulated into a low-profile configuration (not shown) which is suitable for inserting the catheter into a patient percutaneously and passing the working end or distal end 202 of the catheter into a narrow HAS such as a varicose vein. In the low-profile configuration the inner shaft 220, with its electrodes 224, and the umbrella 230, with its ribs 232, are withdrawn proximally into the lumen 212 of the outer shaft 210 such that the electrodes 224 and ribs 232 are contracted radially towards or against the inner shaft 220, and are covered by the outer shaft 210. Where the inner shaft 220 is slidable relative to the umbrella 230, the inner shaft 220 may be withdrawn into the umbrella 230 when the catheter 200 is in the low-profile configuration, such that some portion or all of the electrodes 224 may be received within and covered by both the umbrella 230/membrane 234, and the outer shaft 210. When the catheter 200 is in the low-profile configuration, the atraumatic tip 226 is preferably partially received in and fills the distal opening of the outer shaft, to create an overall smooth atraumatic distal end of the catheter 200.

After insertion of the distal end 212 of the catheter 200 to the treatment site within the HAS, the catheter 200 is manipulated into the deployed, high-profile configuration shown in FIGS. 2-4. To change the catheter 200 to the deployed configuration the outer shaft 210 is withdrawn proximally, and/or the inner shaft 220 and umbrella 230 are advanced distally, to expose the electrodes 224 and ribs 230. (Where the inner shaft 220 is moveable relative to the umbrella 230, the inner shaft may be advanced further distally, to expose the electrodes 224 fully.) Due to their self-expanding properties, the electrodes 224 and ribs 230 attain the expanded configuration on their own after removal of the outer shaft 210. Preferably, the electrodes 224 and ribs 230 are formed from a material such as spring steel or nitinol to ensure sufficient expandability.

As shown in FIG. 2, some or all of the radially outermost portions of the electrodes 224 and ribs 232 are preferably in firm contact with the HAS wall HW when the catheter 200 is in the deployed configuration within the treatment area of the HAS. At this point a micro-perforating jet of high-pressure fluid 40, preferably a tumescent fluid, is conducted through the fluid channels 236 of one or more of the ribs 232, out the rib tip(s) 238, through the HAS wall HW and into the tissue surrounding the HAS. Where the fluid 40 comprises a tumescent agent and/or a bulking agent, the fluid causes swelling and/or bulking of the surrounding tissues such that the HAS walls are constricted, which in turn improves (or causes) apposition of the electrodes 224 with the HAS wall HW.

After any such swelling/bulking takes effect, the HAS (e.g. a varicose vein) is treated with HAS constriction energy delivered by the electrodes 224, to permanently constrict/occlude the HAS. Preferably the HAS constriction energy comprises RF energy. The RF energy is converted within the adjacent venous tissue into heat, and this thermal effect causes the venous tissue to shrink, reducing the diameter of the vein. The thermal effect produces structural transfiguration of the collagen fibrils in the vein. The collagen fibrils shorten and thicken in cross-section in response to the heat from the thermal effect.

The energy causes the vein wall HW to collapse around the electrodes 224. The wall continues to collapse until impeded by the electrodes 224. The electrodes are pressed together by the shrinking vein wall until they touch; and at that point, further collapse or ligation of the wall is impeded. In some embodiments, the catheter 200 is pulled back while energy is applied to the electrode device.

In either bipolar or monopolar operation of the electrode array 222, the application of RF energy is preferably substantially symmetrically distributed through the vein wall, regardless of the diameter of the vein. This symmetrical distribution of RF energy increases the predictability and uniformity of the shrinkage and the strength of the resulting occlusion. The RF energy may be within a frequency range of 250 kHz to 350 MHz; one suitable frequency is 510 kHz. The preferable frequency is 460 kHz.

Optionally, an exsanguinating fluid and/or dielectric fluid can be delivered into the HAS lumen before and during RF heating of the vein. The treatment area of the HAS/vein can be flushed with a fluid such as saline, or a dielectric fluid, in order to evacuate blood from the treatment area of the vein so as to prevent the formation of coagulum or thrombosis. To facilitate delivery of such fluid(s), an additional lumen can be provided in the outer shaft 210 of the catheter 200, or the tip 238 of one or more of the fluid channel ribs 232 can be configured to point distally when deployed, to permit delivery of an exsanguinating fluid and/or dielectric fluid into the HAS lumen and not through the HAS wall HW. However delivered, the exsanguinating/dielectric fluid displaces or exsanguinates blood from the vein so as to avoid heating and coagulation of blood. Fluid can continue to be delivered during RF treatment to prevent blood from circulating back to the treatment site. The delivery of a dielectric fluid increases the surrounding impedance so that RF energy is directed into the tissue of the vein wall. Where present, the membrane 234 of the umbrella 230 facilitates the exsanguination of the treatment area by forming a wall which impedes the migration of blood into the treatment area after the exsanguinating fluid is delivered.

The catheter 200 has a connector (not shown) near its proximal end that has the capability of interfacing with a power source 240. The power source 240 is typically an RE generator, but any other suitable power source may be employed. The proximal end of the catheter 200 may also include appropriate hubs, valves and/or fittings to facilitate fluid communication between the fluid channel ribs 232 and a tumescent fluid source 250.

The electrode array 222 depicted in FIGS. 3-4 comprises a plurality of electrodes 224; if desired, the atraumatic tip 226 can serve as a central electrode. In the depicted embodiment, the electrode array 222 has a diameter of approximately 12 mm when expanded and unconfined, and the distal end of the umbrella 230 has a diameter of approximately 20 mm when expanded and unconfined.

The structure and operation of RF electrode array 222 can, in certain embodiments, be generally similar to the RF therapy apparatus and methods disclosed in U.S. Pat. No. 6,769,433, mentioned and incorporated above.

2) Tumescent Fluid Injected by Needles Combined with RF Electrode Therapy

Figure 7:
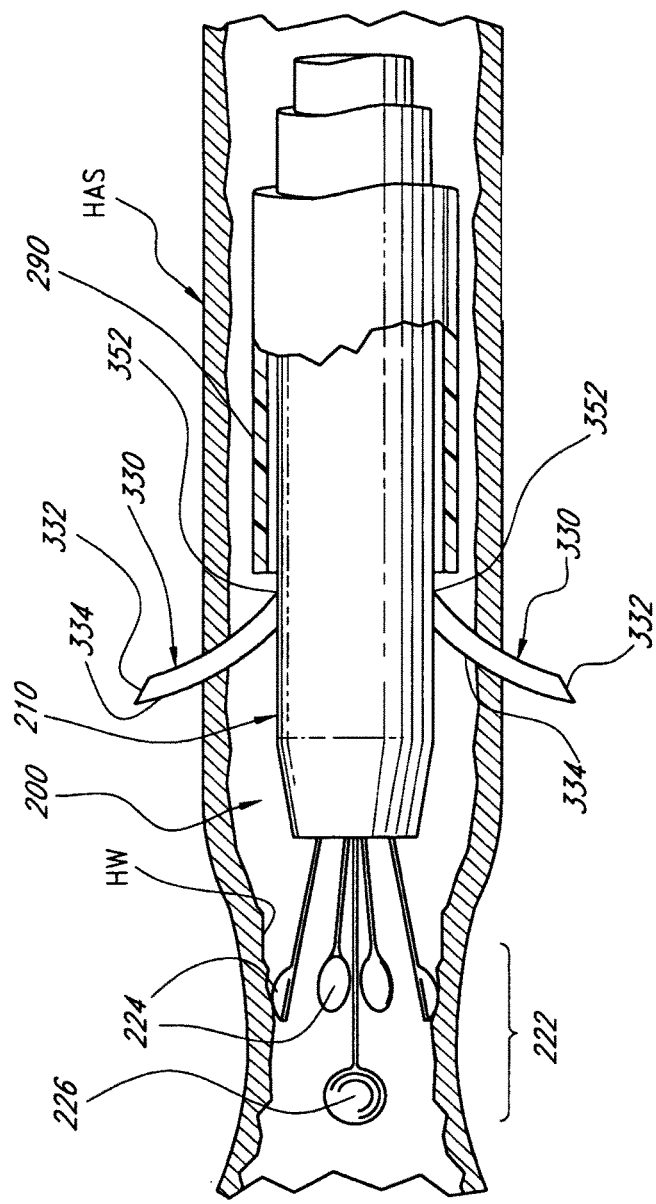
FIG. 7 is a side view of one embodiment of a RF Electrode Therapy device that also delivers tumescent fluids with needles.

In some embodiments, the introduction of tumescent fluids, via one or more needles, from within an HAS to body tissue surrounding an HAS may be combined with a RF Electrode therapeutic device and method. As shown in FIG. 7, the tumescent fluid can be delivered in conjunction with the RF Electrode therapy device such that one delivery device, e.g. the catheter 200 of FIGS. 2-4, modified to incorporate needles 330 as shown in FIG. 7, provides the RF therapy, as well as the tumescent fluid. In this embodiment needles 330, as depicted in FIG. 1 or FIGS. 8-10 and described elsewhere herein, are used to deliver the tumescent fluid into the tissue surrounding the HAS. Preferably, the needles 330 are located within the outer shaft 210 and employ an extension/retraction mechanism similar to that shown in FIGS. 1 and 8-10. In some embodiments, the needles 330 function as electrodes. Preferably, the RF electrodes 224 and the needles 330 are moveable with respect to the outer shaft 210. The needles 330 may be in any location relative to the RF electrodes 224, but it is preferable that they are proximal relative to the RF electrodes 224. The configuration, mechanics and function of the needles 330 can otherwise be generally similar to the device of FIG. 1 or the needles 330 of FIGS. 8-10. Generally, the catheter 200 of FIG. 7 is similar in structure, function and use to the catheter 200 of FIGS. 2-4, except as further described herein with regard to FIG. 7.

Figure 8:
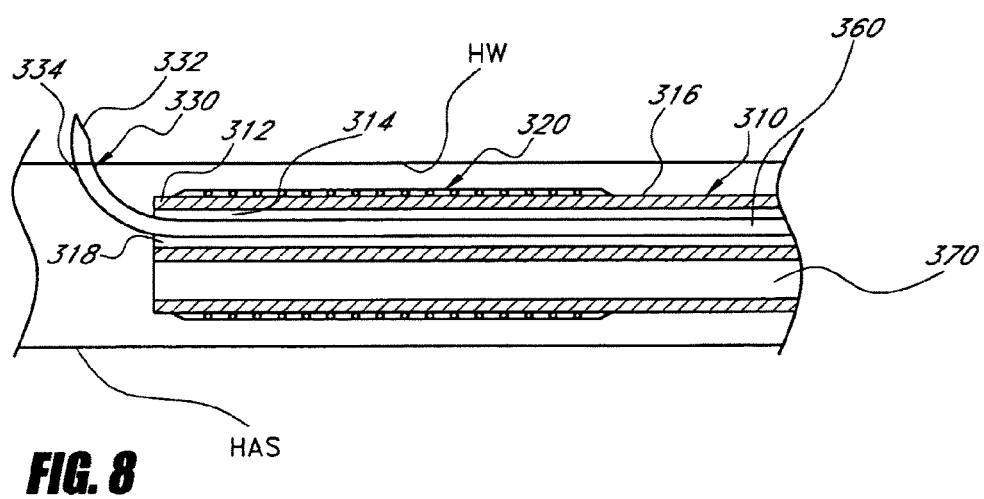
FIG. 8 is a cross-sectional view of one embodiment of a heating coil therapy device that also delivers tumescent fluids with needles that protrude distal of the coil(s).
Figure 9:
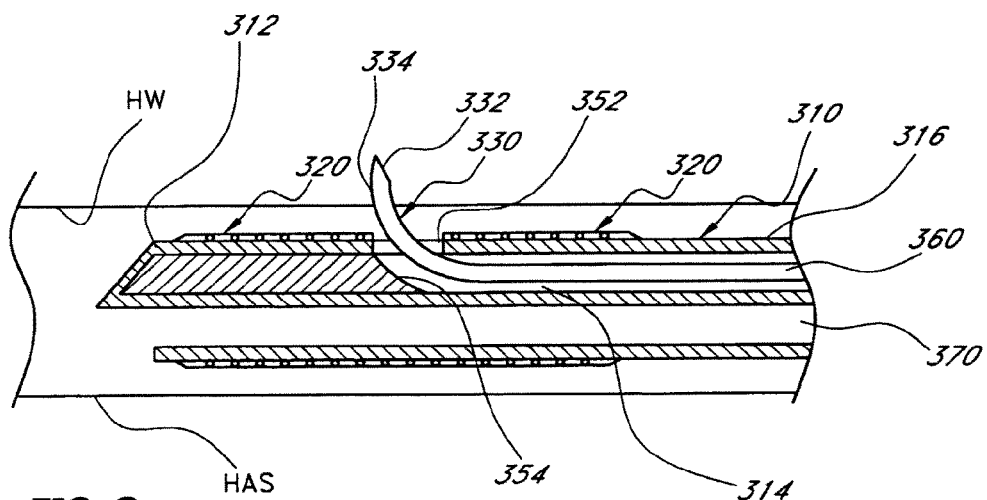
FIG. 9 is a cross-sectional view of another embodiment of a heating coil therapy device that also delivers tumescent fluids with needles that protrude at an intermediate distance along the length of the coil(s).
Figure 10:
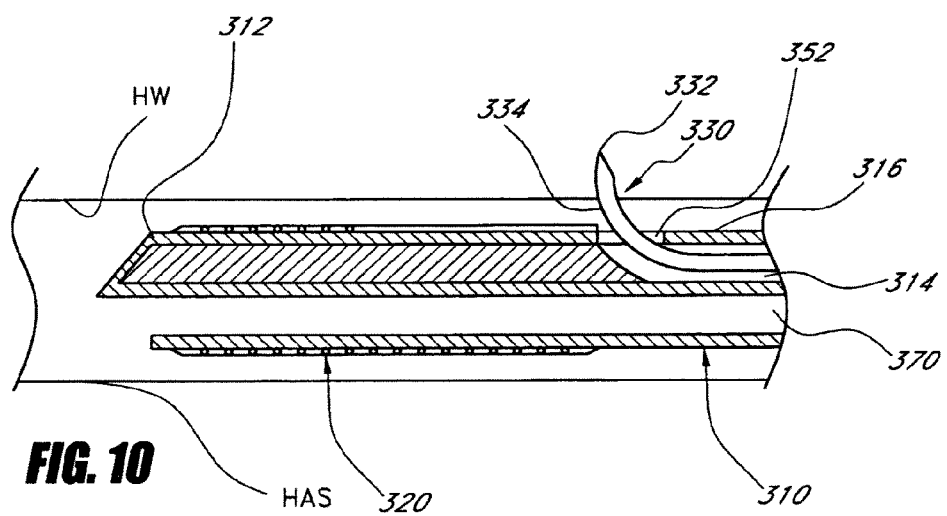
FIG. 10 is a cross-sectional view of another embodiment of a heating coil therapy device that also delivers tumescent fluids with needles that protrude proximal of the coil(s).

The embodiment of the catheter 200 shown in FIG. 7 can be operated to treat an HAS in a manner similar to that described for the catheter 200 of FIGS. 2-4, except that the needles 330 are employed to deliver tumescent fluid (and/or a bulking agent or drug) as described with regard to the embodiment of FIGS. 8-10. The catheter 200 is inserted into a hollow anatomical structure HAS such as the depicted vein. The catheter 200 can further include an external sheath 290 through which the catheter and, if desired, an exsanguinating or dielectric fluid can be delivered to the treatment site in the HAS. In some embodiments, the tumescent fluid or other fluids are delivered through at least one needle 330. In some embodiments, fluid is delivered through a pair of needles 330 positioned on the top end and the bottom end of the catheter 200, as shown in FIG. 7.

B. Heating Coil Therapy Combined with Tumescent Fluid Delivery

In some embodiments, endoluminal tumescent fluid delivery as disclosed herein is used in conjunction with a heating coil therapy system comprising a catheter with a heating coil or other heating element near the distal end thereof, and one or more radially deployable needles for delivering tumescent fluid. In some embodiments, catheter is employed to treat a HAS having an inner wall. Preferably, the heating element has a length and a width measured orthogonal to its length; its length is preferably greater than its width. The catheter may be placed in a first position within the HAS and the needle(s) deployed to deliver tumescent fluid endoluminally through the HAS wall near the first position. After the tumescent fluid takes effect, the heating element may be operated to emit heat from substantially all of its length into the inner wall of the HAS at the first position. In some embodiments, the element is subsequently moved, after emitting heat in the first position, to a second position within the HAS by a longitudinal or axial distance corresponding to approximately the heating coil's length. In some embodiments, the distance is approximately equal to the length of the heating coil minus a desired overlap distance. While the catheter is stationary in this second position, the needles are deployed and used to deliver tumescent fluid near the second position. After the tumescent fluid takes effect in the second position, the heating element is again operated and again emits heat into the inner wall along substantially the length of the element. Therapy performed with a heating element for HAS treatment is described in more detail in U.S. Provisional Application No. 60/780,948, filed Mar. 9, 2006, entitled SYSTEMS AND METHODS FOR TREATING A HOLLOW ANATOMICAL STRUCTURE, which is hereby incorporated by reference herein and made a part of this specification.

1) Tumescent Fluid Injected by Needles Combined with Heating Coil Therapy

FIGS. 8-10 depict several embodiments of an HAS treatment catheter 300 which generally comprises a catheter shaft 310, one or more heating elements 320 disposed on the shaft 310, and one or more radially expandable or deployable needles 330 which can be employed to deliver tumescent fluid through an HAS wall HW. The heating element 320 is preferably disposed on an outer surface of the shaft 310, and preferably at or near a working end or distal end 312 of the shaft. In the depicted embodiment, the heating element 320 comprises an electrically resistive coil, but in alternative embodiments any other suitable heat-emitting device may be employed, such as other electrically resistive heaters, a fluid-conducting heat exchanger, a chemical reaction chamber, etc. In other embodiments, one or more electrodes or RF electrodes (including but not limited to the electrode array 222 disclosed herein) can be disposed on the shaft 310 at or near the distal end thereof, and employed to treat an HAS with RF energy as described herein.

The needle(s) 330 are moveable from a retracted position (not shown) in which each needle 330, including each needle tip 332 thereof, is withdrawn into a needle lumen 314 of the shaft 310, to a deployed or radially expanded position as shown in FIGS. 8-10 wherein the tip 332 of each needle is displaced radially outward from the longitudinal axis of the catheter shaft 310, and radially outward from the sidewall 316 of the shaft 310. When the distal end 312 of the catheter 300 is positioned within a lumen of an HAS as depicted, movement of the needle(s) 330 to the deployed position can cause the needle(s) to penetrate the HAS wall HW such that the needle tip(s) 332 are disposed in the tissue surrounding the HAS.

The deployment and retraction of the needle(s) 330 is preferably accomplished by distal and proximal movement, respectively, of each needle 330 along the corresponding needle lumen 314. As each needle 330 is moved distally, the needle tip 332 thereof emerges from the corresponding lumen 314 and moves radially away from the longitudinal axis of the shaft 310. In one embodiment, each needle 330 has a heat-set distal curve 334 which prevails when the needle end is unconstrained, such as when the needle end is urged near the end of the needle lumen 314. Such a heat-set curve is straightened when the needle is withdrawn into the lumen.

In the embodiment of FIG. 8, the needle lumen 314 terminates in an axially-facing lumen opening 318 distal of the heating element 320, which petinits the needle end to curve and extend radially, distal of the heating element 320, as the needle end emerges from the lumen opening 318. Thus the needle tip 332 can be directed toward and penetrate the HAS wall HW at a penetration location distal of the heating element's position within the HAS.

In the embodiment of FIG. 9, the needle lumen 314 terminates in a radially-facing sidewall port 352, and an optional ramp 354 can be provided to urge the needle tip 332 in the radial direction as the needle 330 is urged distally. Thus the needle tip 332 emerges radially from the port 352 and moves toward and penetrates the HAS wall HW. In this embodiment, and in the embodiment of FIG. 10, no heat-set curve 334 is believed necessary to facilitate radial movement of the needle tip 332, although such a curve may be employed in any event. The port 352 and ramp 354 are positioned midway along the length of the heating element 330 so that the needle tip 332 can be directed toward and penetrate the HAS wall HW at a penetration location coincident with the heating element's position within the HAS, facilitating accurate injection of tumescent fluid.

The embodiment of FIG. 10 is generally similar to that shown in FIG. 9, with the exception that the port 352 and ramp 354 are positioned proximal of the heating element 330 so that the needle tip 332 can be directed toward and penetrate the HAS wall HW at a penetration location proximal of the heating element's position within the HAS. In the embodiments of FIGS. 9 and 10, the ramp 354 can be formed by the proximal end of a filler plug that occupies the distal extremity of the needle lumen 314.

In one embodiment, injection tubing 360 extends proximally from each the needle 330, towards the proximal end of the catheter 300 to provide fluid communication between the needle 330 and a source of tumescent fluid (not shown).

Preferably, each needle 330 has a beveled and sharp tip 332 at the distal end thereof. The needle tip(s) 332 may be beveled in any direction so as to introduce fluid in a desired direction. In some embodiments, the needle has a sharp tip with a fluid delivery port on the tip, facing axially relative to the longitudinal axis of the needle, or alongside the tip, facing radially relative to the longitudinal axis of the needle. The preferred direction of the bevel can vary depending on the location of the coil(s) 320 with respect to the location of the needle(s) 330, so as to direct the tumescent fluid toward the area to be treated with the coil.

As seen in FIGS. 8-10, the shaft 310 preferably includes a guidewire lumen 370 to facilitate insertion of the catheter 300 into an HAS over a previously-inserted guidewire (not shown).

In some embodiments of the catheter 300, multiple needle(s) 330 are employed which extend from positions spaced at radially-separated intervals (e.g., at the 12 o'clock, 4 o'clock and 8 o'clock positions as the shaft 310 is viewed axially). In embodiments where multiple needles are employed, the needles can extend from positions that are longitudinally spaced along the shaft 310, including any one or combination of the various positions identified relative to the heating coil 320 and depicted in FIGS. 8-10. Furthermore, the catheter 300 could include multiple sets of expanding needles which are radially spaced about the shaft 310 as detailed above, with the needle sets spaced apart along the length of the shaft 310.

In certain embodiments, the heating element 320 is an electrically resistive heating element, including but not limited to any of those described elsewhere herein. For example, the heating element may comprise a single, bifilar or other electrically resistive wire. Certain embodiments of the heating element 320 comprise a wire having tightly-wrapped coils around a hollow, elongate structure. The heating element may comprise a loose, tight, or variable-pitch coil wound around a solid or hollow elongate structure.

In certain embodiments, the heating element 320 has a substantially short axial length. For example, in certain embodiments, the heating element has a length of between approximately one centimeter and approximately ten centimeters. Such a length is believed to be particularly advantageous for embodiments utilizing manual, external compression to treat a HAS. In certain preferred embodiments, the length of the heating element 320 is approximately seven centimeters.

In certain embodiments, the heating energy delivered by the heating element 320 is less than 100 watts. In a more preferred embodiment usable in an indexing process, the heating energy delivered by the heating element 320 is between approximately five watts and twenty watts.

Thus, in some embodiments an HAS treatment catheter has a catheter shaft which extends from a proximal end to a distal end thereof; a therapeutic energy source located at or near a distal end of the shaft; and at least one fluid delivery channel located in the shaft. The therapeutic energy source can comprise an electrode or a resistive heating element, or any other suitable energy source. In some embodiments, as illustrated in FIG. 8, the therapeutic energy source is a heating coil element. The fluid delivery channel located in the shaft has a channel having a delivery tip which is movable from a retracted position near a longitudinal axis of the shaft, to a deployed position farther from the longitudinal axis. In some embodiments, such as the embodiments illustrated in FIGS. 8-10, the fluid delivery channel comprises at least one needle.

In use, the catheter 300 is inserted into an HAS such that the distal portion of the catheter, including the heating element 320 or electrode(s), are in the intended treatment area of the HAS. Once the catheter is properly positioned, the needle(s) 330 are extended as shown in FIGS. 8-10, so that the needles penetrate the HAS wall HW and the needle tips 332 are disposed within the tissue surrounding the HAS. Tumescent fluid and/or a bulking agent is then conducted from an external tumescent fluid source or bulking agent source to the needles, and then injected out the tips of the needles into the target tissue, which swells and/or bulks in reaction to the fluid/agent which is injected. (In some instances, sufficient time should be allotted for tumescent fluid to take effect. In some embodiments, the HAS therapy technique will last for a short duration in comparison to the time necessary for the tumescent fluid to be injected and to take effect. Additionally, the tumescent fluid is preferably distributed evenly along the fascial envelope around the HAS/vein in order to affect the target portion of the vein.)

Contemporaneously with injection of the tumescent fluid or bulking agent, or after some time interval has passed after injection and retraction of the needle(s) (e.g. to permit the fluid/agent to take effect and cause constriction of the HAS near the heating element 320), power is applied to the heating element 320 (or electrodes). The heating element 320 emits heat into the adjacent portions of the HAS wall HW, which preferably has reduced in diameter by virtue of the injection and is in good thermal contact with the heating element. The heat emitted into the HAS wall in turn causes the wall to shrink, reducing the diameter of the HAS. The thermal effect produces structural transfiguration of the collagen fibrils in the wall. The collagen fibrils shorten and thicken in cross-section in response to the heat from the thermal effect, causing the HAS wall HW to collapse around the heating element 320. Thus is formed a durable occlusion in the HAS. After heat has been emitted for a sufficient time, the heating element 320 is turned off (and the needles retracted if still in the expanded position) and withdrawn or moved to a second treatment position within the HAS.

In some embodiments, the heating element 320 is progressively moved through the HAS in a series of discrete steps from a first position to a final position in order to treat a desired contiguous length of the HAS. The process of moving a heating element through an HAS in a series of discrete steps during treatment is referred to herein as "indexing."

A general indexing process may proceed by advancing the heating element 320 to a distal-most position, injecting tumescent fluid and/or a bulking agent with the needle(s) 330, and applying power to the heating element while the heating element remains stationary at the distal-most position. The temperature of the subject heating element is allowed to ramp up or increase to a desired temperature and remains in place for a desired dwell time, e.g. 25 seconds. Once the desired dwell time is reached (e.g., the treatment for the section is completed), the heating element can be powered down, and the element can be indexed proximally to a second position, at which point at least one of the injection, ramp up, dwell, power down, and indexing procedures may be repeated.

In certain embodiments, in order to accurately index the heating element 320, it is desirable to provide a means for repeatedly moving (or facilitating accurate, repeated movement of) the heating element proximally within an HAS undergoing treatment by a desired distance. In certain embodiments, this desired distance is less than the overall length of the heating element so as to effectively re-treat regions that may receive less heat energy as a result of an uneven heating profile along the axial length of the heating element. It may also be desirable to treat more than once an initial and/or final treatment region of the HAS in order to arrange for start- and endpoints of the indexing distances to correspond with catheter shaft markings or to arrange that, after the full series of indexed treatments, the final HAS treatment region is in substantial alignment with the end of the introducer sheath. In addition, in certain embodiments, the system includes means for preventing the heating element from being powered up while it is within the introducer sheath.

In certain embodiments, the catheter shaft 310 may comprise a plurality of markings not shown along the axial length thereof, proximal of the heating element 320, in order to facilitate visual verification of indexing positions. Such markings advantageously assist a user in positioning and indexing the heating element 320 of the catheter 300 during treatment. For example, the user may determine from the markings how far the heating element 320 should be retracted during a treatment interval.

In certain embodiments, the physician uses the markings to manually and selectively move the catheter 300 within a HAS of a patient. For example, the heating element 320 of may extend approximately seven centimeters in length. In such an embodiment, the markings may be spaced apart at approximately 6.5 centimeter intervals along the shaft 310. When treating the patient, the physician may use the markings to manually withdraw from the HAS the catheter 300 at 6.5 centimeter intervals between successive inject-and-heat treatments of the HAS. Such a 6.5 cm movement can be performed by proceeding from a first state in which a first shaft marking is aligned with a fixed reference point (e.g., the proximal edge of the introducer sheath hub or other datum device), then moving the catheter shaft 310 proximally (or distally) to reach a second state in which a proximally (or distally) adjacent second shaft marking is aligned with the fixed reference point. In other embodiments, a device may be used to automatically withdraw the catheter at the predetermined intervals indicated by the markings.

Figure 11:
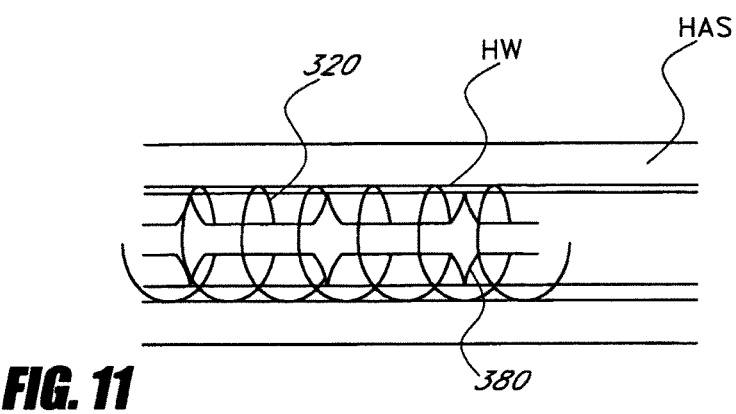
FIG. 11 is a side view of another embodiment of a heating coil therapy device that also delivers tumescent fluids with needles.
Figure 12:
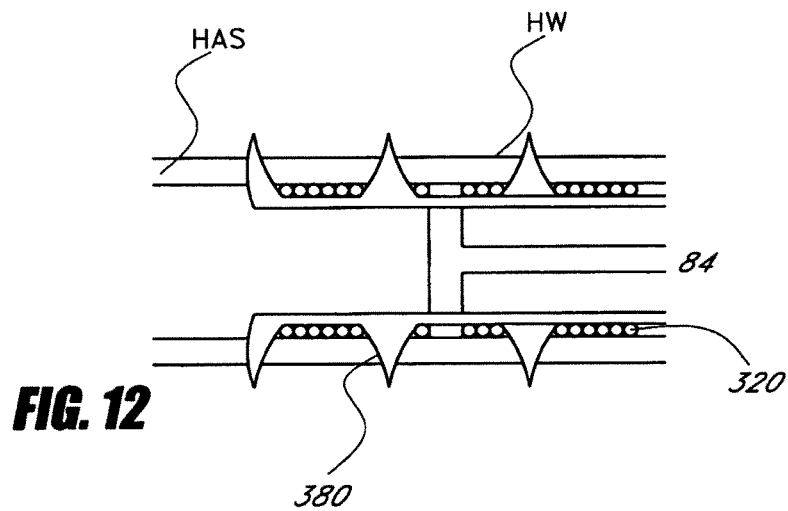
FIG. 12 is a side view of another embodiment of a heating coil therapy device that also delivers tumescent fluids with needles.

In further embodiments as shown in FIG. 11, the heating coil 320 may comprise a flexible and "free" spring coil 320 which is deployed in the HAS lumen and permitted to form a helix which conforms to the HAS inside diameter. An array of needles in the form of spikes 380 can be located radially within the spring coil 320. The spikes 380 are configured to penetrate the HAS wall HW and introduce tumescent fluid into the surrounding tissue. The spikes 380 may penetrate the HAS wall HW when the HAS wall HW and spring coil 320 are compressed down to a diameter that is less than the diameter or width of the spikes (which compression changes the coil 320 from the relaxed configuration shown in FIG. 11 to the collapsed configuration shown in FIG. 12). In some embodiments, the HAS walls may be compressed by applying a vacuum to the interior of the HAS such that the force of the vacuum collapses the HAS walls HW and spring coils 320 to a smaller diameter, thereby impaling the spikes 380 through the HAS walls HW to introduce the tumescent fluids into the surrounding tissue. Instead of or in addition to application of a vacuum, the tissues surrounding the HAS may be manually compressed onto the spikes 380 by applying extracorporeal, manual pressure or applying a tight bandage above or around the location of the coil 320 and spikes 380. (In general, compression of the HAS diameter down to a diameter less than the outside diameter of the tumescent fluid delivery needles or spikes is also assisted by delivery of the tumescent fluid itself which acts to compress and exsanguinate the HAS as it fills the fascial envelope.) Heat is then generated with the coil 320 in the usual manner to cause a durable occlusion of the HAS.

2) Pressurized Tumescent Fluid Combined with Heating Coil Therapy

In some embodiments, the delivery of tumescent fluid to body tissue by high-pressure is combined with the heating coil or heating element therapy. These pressure jets can be in any location relative to the coil(s). In some embodiments, the action of the pressure jets penetrating the vein wall is improved by compressing the vein against the catheter during fluid jetting.

With regard to the embodiment of FIGS. 2-4, an HAS constriction energy source in the form of one or more heating elements can be disposed on the inner shaft 220 or outer shaft 210, and preferably at or near a working end or distal end of the shaft 220/210. In one embodiment, the heating element comprises an electrically resistive coil, but in alternative embodiments any other suitable heat-emitting device may be employed, such as other electrically resistive heaters, a fluid-conducting heat exchanger, a chemical reaction chamber, etc. The heating element employed on the shaft 220/210 can be generally similar to the various embodiments of heating elements discussed elsewhere herein. Additionally, where a heating element is employed the proximal portion of the shaft 220/210 may include indexing marks as discussed elsewhere herein to facilitate "indexed" operation of the heating element to treat an HAS.

C. Perforator Vein Therapy Combined with Tumescent Delivery

In some embodiments the delivery of tumescent fluid may be accomplished in combination with perforator vein therapy. In some embodiments of perforator vein therapy, constricting a target HAS comprises percutaneously introducing a distal end of a probe 400, such as those depicted in FIGS. 13 and 14, to a location in the HAS and delivering energy into the target HAS to constrict the target region of the HAS. In some embodiments the probe 400 is stiff and in other embodiments the probe 400 is flexible. The probe 400 may be introduced by advancing a sharpened distal end thereof through tissue directly to the target region, by positioning a sheath through tissue to the target region and advancing the probe through the sheath, or by positioning a guidewire through a needle, removing the needle, and advancing the probe over the guidewire to the location near the target HAS. In some embodiments, the probe is inserted within the target HAS and therapy is applied to the inner wall. Perforator vein therapy may utilize RF electrodes, heating coils, as well as other sources of therapeutic energy.

1) Pressurized Tumescent Fluid Combined with Perforator Vein Therapy

Perforator veins connect the deep venous system of a leg to the superficial venous system or surface veins which lie closer to the skin. Normal or healthy perforator veins pass blood from the surface veins to the deep veins as part of the normal blood circulation. Incompetent perforator veins allow blood flow from the deep venous system to the surface veins, causing or contributing to problems, such as varicose veins, edema, skin and soft tissue changes, lipodermatosclerosis, chronic cellulites, venous ulcers, and the like.

Figure 13:
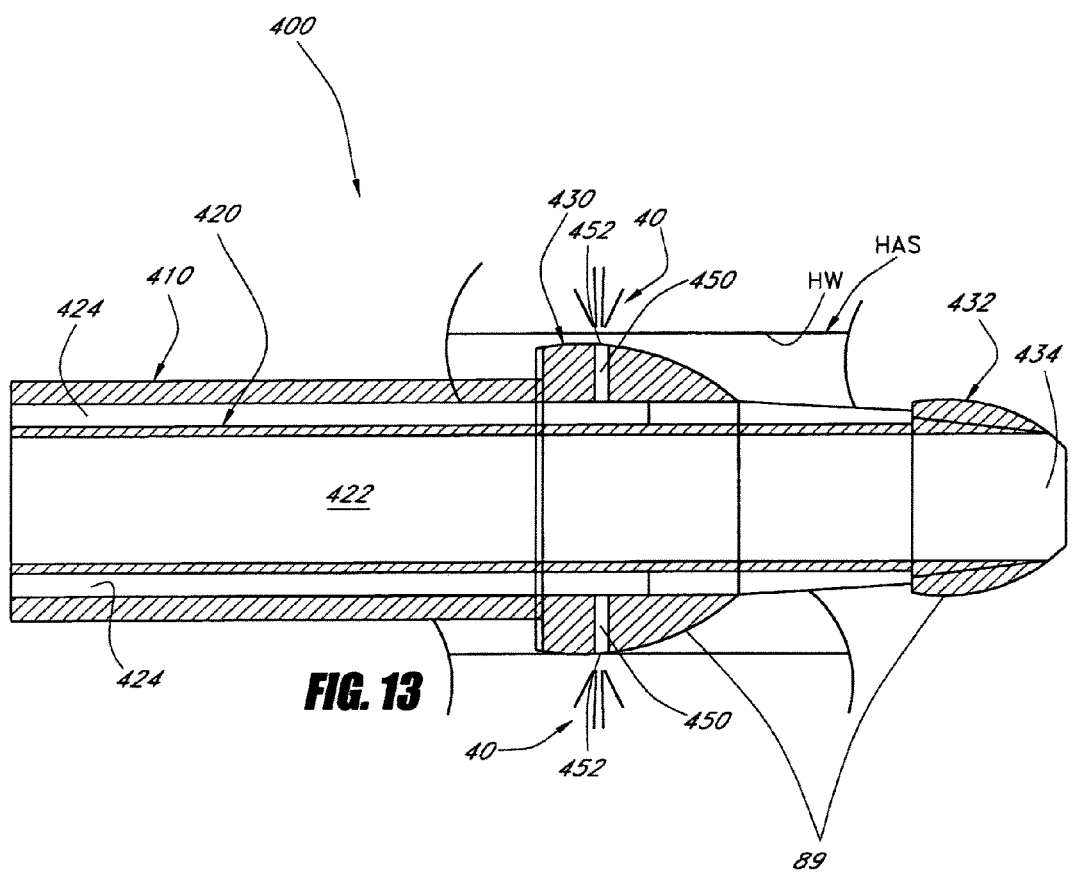
FIG. 13 is a side view of one embodiment of a perforator vein RF Electrode therapy device that also delivers tumescent fluids.

FIG. 13 depicts one embodiment of a probe 400 which can be used to perform perforator vein therapy and which includes features to introduce high pressure tumescent fluid such that it penetrates the walls of a HAS in which the probe is inserted and reaches the surrounding body tissue. The probe 400 generally comprises an outer shaft 410, an inner shaft 420 which is received within and generally coaxial with the outer shaft 410, and a pair of proximal and distal electrodes 430, 432 positioned at the distal end of the shafts. Preferably the distal tip 434 of the distal electrode 432 forms an opening to a lumen 422 of the inner shaft 420.

An annular space 424 is formed between the outer and inner shafts 410, 420 and provides a fluid flow path from a proximal end (not shown) of the probe 400 to one or more fluid injection channels 450 formed in the proximal electrode 430. Alternatively, the inner shaft 420 may be shorter than and bonded to the outer shaft 410 near the distal end with the fluid injection channels 450 traversing through both shafts to the inner lumen of the inner shaft 420 (in this case the distal tip 434 would be permanently closed or plugged with a removable feature). Thus a high-pressure fluid 40, such as a tumescent fluid, bulking agent, drug, etc. can be delivered from a source of the fluid/agent/drug (not shown) in fluid communication with the annular space 424 and injection channels 450, distally down the annular space 424, through and out the injection channels 450 and into an adjacent HAS wall HW. To facilitate good apposition of the outermost ends or ports 452 of the injection channels 450 against the HAS wall HW, the channels 450 and outermost ends 452 are preferably positioned in a locally radially outermost region of the electrode 430. (Alternatively, the channels 450 can extend through the outer shaft 410 proximal of the electrodes 430, 432; if so, the channels 450 and outermost ends or ports 452 are preferably positioned in a locally radially outermost region of the shaft 410.)

In use, the probe 400 is inserted into an HAS or perforator vein percutaneously and the distal portion thereof is maneuvered into the desired treatment location within the HAS. Once the probe is properly positioned, pressurized fluid (e.g. tumescent fluid) is conducted from a fluid source, distally down the annular space 424 (in this embodiment), through the channels 450 and out the ports 452. The pressurized fluid penetrates through the adjacent HAS wall HW, and spreads into the tissue surrounding the HAS. This causes the tissue to swell and constrict the HAS wall HW such that the electrodes 430, 432 are in close apposition to the HAS wall. An electrical current, such as an RF electrical current, is then applied to the electrodes 430, 432 so that RF energy is passed through the HAS wall near the electrodes. As discussed elsewhere herein, the RF energy heats the HAS wall, causing a durable shrinkage and ligation or occlusion of the HAS. The probe can be drawn proximally as the energy is applied to the tissue, treating an extended length of the vein to form a long ligation or occlusion.

Additionally, the probe 400 can be employed to treat quadrants of the HAS or vessel sequentially. The probe 400 is tilted toward one quadrant of the vessel and used to treat the selected quadrant and then tilted toward the next quadrant of the vessel and used to treat that quadrant, which cycle is then repeated to affect 360 degrees of the vessel diameter at the treatment location. For example a first quadrant at a 0 degrees position for 1 minute of RF energy application, a second quadrant at a 90 degrees position for 1 minute of RF energy application, a third quadrant at a 180 degrees position for 1 minute of RF energy application, and a fourth quadrant at a 270 degrees position for 1 minute of RF energy application. After treating around the vessel wall circumference at one location in this manner, the probe is advanced longitudinally to another location where the circumference is again treated in this sequential-quadrant manner. An injection of tumescent fluid is preferably made with the probe 400 before some or all of the sequential-quadrant treatment cycles.

In some embodiments, the probe 400 is operated in a bipolar mode to constrict a target perforator vein. As illustrated in FIG. 13, the probe 400 is rigid but it could also have flexible shafts 410, 420. The probe 400 can be inserted into the HAS/vein through an introducer sheath or cannula, but alternatively the insertion can be performed by "directly" penetrating the vein with a probe 400 having a needle or trocar in the central lumen 422 or having a sharpened distal electrode 432. After insertion of the probe, the electrodes are energized as the probe is drawn back to contact the opposite side of the vein or other HAS. The vein or other HAS is heated and collapsed as the probe is continued to be drawn back through the HAS. As probe is withdrawn, the perforator vein or other HAS is constricted; if desired, the sequential-quadrant treatment procedure described above is employed. The procedure could also be performed using a single polarity and/or electrode device. Additionally, the protocol illustrated could also be used in performing an extravascular procedure.

Figure 14:
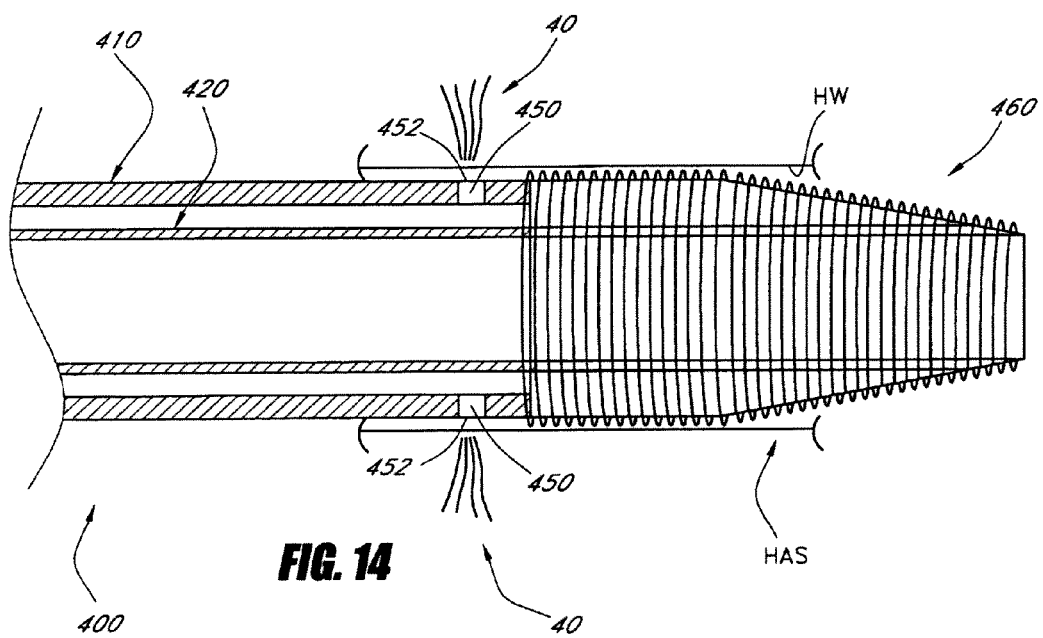
FIG. 14 is a side view of one embodiment of a perforator vein heating coil therapy device that also delivers tumescent fluids.

FIG. 14 depicts another embodiment of the probe 400 that can be generally similar to the probe 400 of FIG. 13, except as further discussed below. Instead of or in addition to the electrodes, the probe 400 of FIG. 14 includes a heating element 460 at or near the distal end of the shafts 410, 420. The depicted heating element is a resistive heating coil, but alternatively any other suitable electrically driven heating element may be employed, or a non-electrical heating element such as a fluid-conducting heat exchanger, chemical reaction chamber, etc. The injection channels 450 preferably extend through the outer sheath 410 proximal of the heating element 460, but the channels may alternatively be positioned midway along the heating element 460, passing between adjacent turns of the coil. The probe 400 of FIG. 14 is used to treat an HAS or perforator vein in the same manner as the probe 400 of FIG. 13, with the exception that the heating element 460 is energized to emit heat into the adjacent HAS wall HW after injection of tumescent fluid thereinto. In one embodiment, the probe 400 of FIG. 14 is used to treat an HAS in an "indexing" fashion as described elsewhere herein. As a further alternative, the probe 400 of FIG. 14 can be employed in a sequential-quadrant HAS treatment method as described above.

Figure 15:
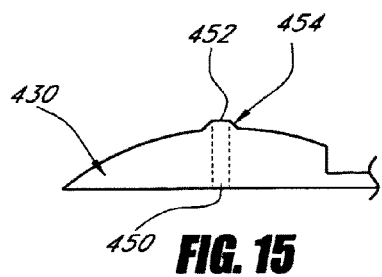
FIG. 15 is a side view showing one embodiment of protruding tumescent injection holes of the device of FIG. 14.
Figure 15A:
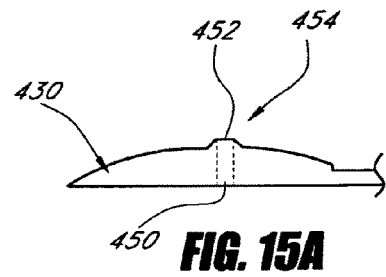
FIG. 15A is a side view showing another embodiment of protruding tumescent injection holes of the device of FIG. 14.

With reference to FIGS. 15 and 15A, in some embodiments of the probe 400 of FIGS. 13-14, the ports or outermost ends 452 of the injection channels 450 are located on protrusions 454 which protrude outwardly from the adjacent areas of the surface of the electrode 430, or which protrude outwardly from the adjacent areas of the sidewall of the outer shaft 410 (where the channels 450 in question extend through the shaft 410). The protrusions 454 encourage tissue penetration by the fluid, etc.

Delivery of the tumescent fluid, etc. is preferably at high pressure. The pressure may be dependent upon the pressure loss along the length of the catheter and the pressure drop at the orifice or needles. For example, in one embodiment, pressures may range from 100 to 1000 psi. In some embodiments, the pressure exceeds 1000 psi. In some embodiments, the pressure applied is provided by a pump, such as a pump comprised of HPLC columns.

Further details on the probe 400 can be found in U.S. Patent Application Publication No. 2006/0030849A1, published on Feb. 9, 2006, titled METHODS AND APPARATUS FOR COAGULATING AND/OR CONSTRICTING HOLLOW ANATOMICAL STRUCTURES. The entirety of this publication is hereby incorporated by reference herein and made a part of this specification.

2) Tumescent Fluid Injected by Needles Combined with Perforator Vein Therapy

Figure 18:
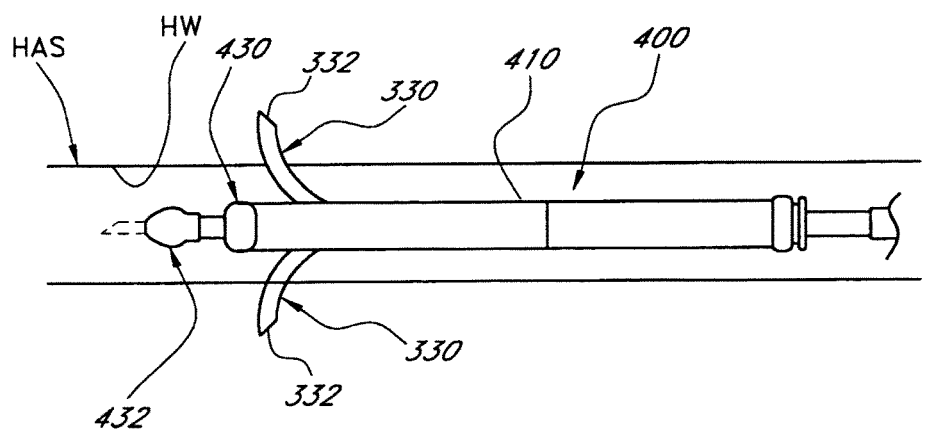
FIG. 18 is a partial side view of another embodiment of a perforator vein therapy probe that uses needles to introduce tumescent fluids.

In some embodiments, as seen in FIG. 18, the perforator vein therapy probe 400 includes one or more fluid injection needles 330. The needles 330 can be generally similar in structure and function to the needles 330 of FIGS. 8-10, to introduce tumescent fluid, a bulking agent, drugs, etc. into the tissue surrounding the HAS. Preferably, the needles 330 are located within the probe 400 and are configured to extend beyond the probe 400 to inject tumescent fluid into body tissue. Thus, the probe 400 of FIG. 18 can be employed to treat an HAS in a similar manner as the probe 400 of FIG. 13, with the exception that the needles 330 are employed to inject tumescent fluid. For this portion of the treatment procedure, the needles are operated in a manner similar to the needles 330 of FIGS. 8-10. Accordingly, the probe 400 may be connected to a source of tumescent fluid (not shown) so that the needles 330 are in fluid communication with the source.

Figure 16:
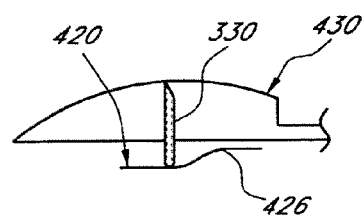
FIG. 16 is a partial side view of one embodiment of a perforator vein RF Electrode therapy device that uses needles to introduce tumescent fluids.
Figure 16A:
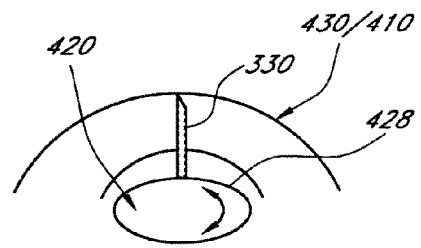
FIG. 16A is a perspective view of one embodiment of a perforator vein RF Electrode therapy device that uses needles to introduce tumescent fluids.
Figure 17:
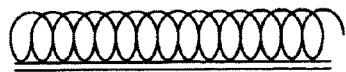
FIG. 17 is a partial side view of one embodiment of a perforator vein heating coil therapy device that uses needles to introduce tumescent fluids.
Figure 17:
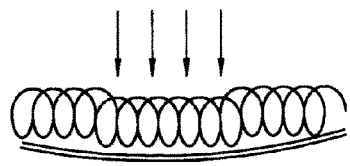
Figure 17A:
FIG. 17A is the device of FIG. 17 with the needles penetrating the HAS walls.
Figure 17A:
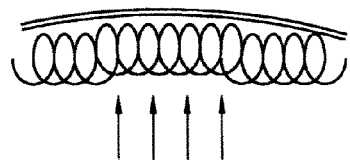

In some embodiments, the needles 330 are extendable and retractable along a generally straight path through the electrode 430 or outer shaft 410, as depicted in FIGS. 16 and 16A. In these embodiments, extension and retraction of the needles 330 can be accomplished by a manipulation of the distal electrode 432 and/or a moveable embodiment of the inner shaft 420 coupled thereto, or with some other actuator shaft. For example axial or longitudinal movement of the electrode 432 and/or inner shaft 420 may extend and/or retract the needles as depicted in FIG. 16 (via ramp 426), and rotational movement may extend and/or retract the needles as depicted in FIG. 16A (via cam 428). In other embodiments, a needle or multiple needles may be rigidly fixed while the surrounding shaft is deflected causing the needles to penetrate the HAS wall and extend into the surrounding body tissue, as seen in FIGS. 17 and 17A. Preferably, this may be accomplished by external compression of the tissue which would also enable the needles to penetrate the HAS walls HW.

III. Delivery of Tumescent Fluid Outside of HAS

Figure 19:
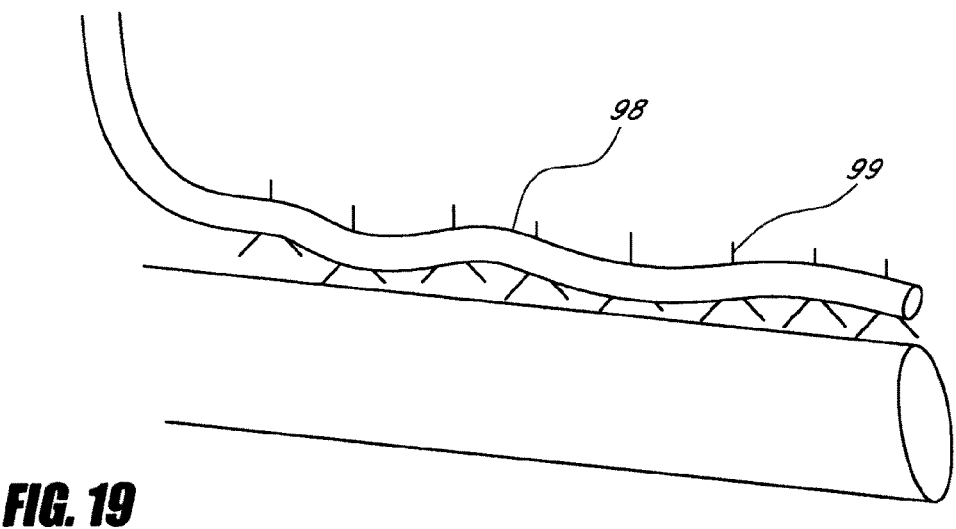
FIG. 19 is a perspective view of one embodiment of a device that delivers tumescent fluids from outside the HAS.
Figure 19A:
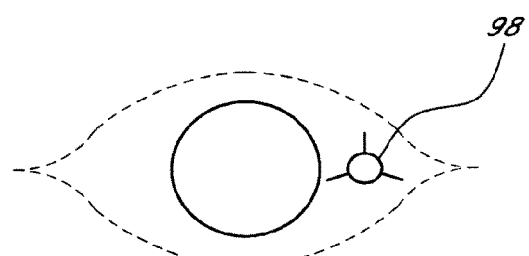
FIG. 19A is a front view of the device of FIG. 19 with a fascial envelope depicted.
Figure 19B:
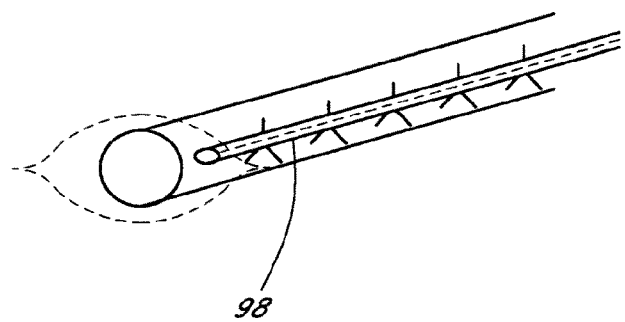
FIG. 19B is perspective view of the device of FIG. 19 with a fascial envelope depicted.

In some embodiments, tumescent fluid is delivered from outside the HAS. In one "garden hose" technique, a large volume of tumescent fluid is introduced to the fascial envelope along the length of the targeted body tissue. In other embodiments, air pressure could be used to inject high pressure tumescent fluid from outside the body. In other embodiments a flexible insertion tube with a sharp distal end is inserted through the skin and guided to the desired location. In other embodiments, the tumescent fluid is delivered by a needle inserted to a location near the targeted body tissue. Preferably, a needle or delivery tube is inserted through the skin to reach the targeted body tissue, and tumescent fluid is introduced when the needle or delivery tube reaches a desired location. See FIGS. 19, 19a, and 19b. In some embodiments, the device inserted through the skin is extended and retracted by mechanical means. For example, a threaded hub located near the proximal end of the device could mate with a threaded luer that is rotated to extend and retract the device. In some embodiments, one or more tumescent needles is incorporated into an access shaft, providing the needles with the ability to access the fascial envelope.

Preferably, the tumescent fluid 99, which is depicted by the lines extending from the delivery tube 98, is introduced to the fascial envelope, which is the space surrounding a vessel. See FIGS. 19, 19a, and 19b. In some embodiments, tumescent fluid 99 is introduced in one location relative to the HAS and then is mechanically pushed along the length of the HAS, such as through manual compression and/or massage (i.e. massaging the tissue by hand through the patient's skin). The tube may also be configured with a pump to introduce the tumescent fluid.

Figure 20:
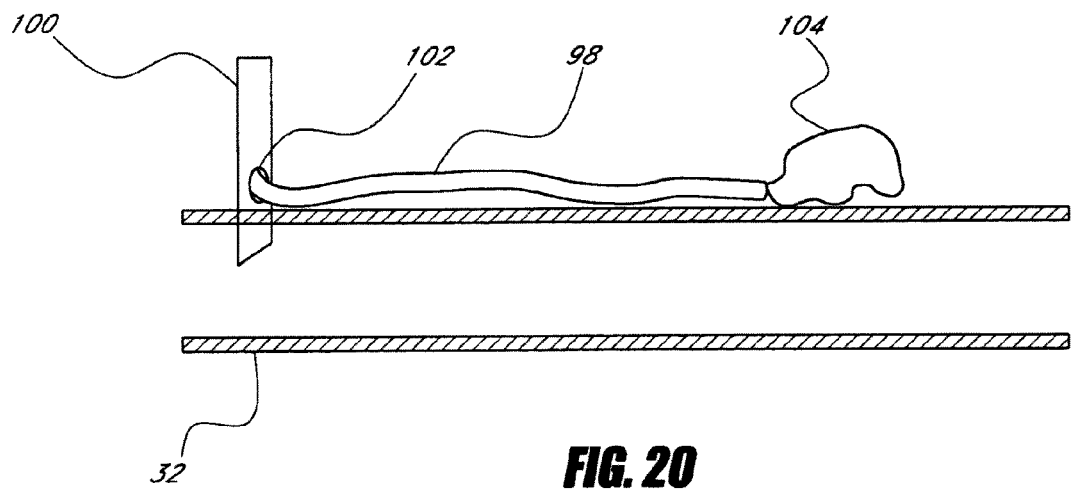
FIG. 20 is a side view of another embodiment of a device that delivers tumescent fluids from outside the HAS.

In some embodiments, a tumescent fluid delivery hole 102 is located a distance proximal relative to the tip of a needle 100 inserted within body tissue, as shown in FIG. 20. Preferably, the tumescent fluid 104 is released through the delivery hole 102 into body tissue surrounding the HAS walls 32. In other embodiments, a delivery tube 98 can be extended through the delivery hole 102 to deliver tumescent fluid 104 a distance from the delivery hole 102. Furthermore, the delivery tube 98 may be movable with respect to the needle 100 such that it can be extended and retracted within the fascial envelope along the length of the HAS to introduce tumescent fluid 104 along a greater length of the HAS. In further embodiments, the delivery tube 98 may be configured with multiple tumescent fluid delivery points along its length and around its perimeter. This would allow simultaneous tumescent fluid delivery along a greater length of the HAS. Additionally, a rod may be inserted through the delivery tube 98 to stiffen the delivery tube 98 during placement.

In some embodiments, impedance is used to indicate the location of the delivery hole with respect to the HAS. This may be accomplished with a sensing electrode at the distal end of the needle. Preferably, this assists in determining whether the needle tip is inside or outside the HAS and the corresponding location of the delivery hole. For example, the needle may be pushed within the body tissue until the impedance drops, which may indicate the delivery hole is in the desired location to deliver tumescent fluid. In one embodiment, the delivery hole is outside the HAS when the needle has penetrated the HAS. In one embodiment, the steps to accomplish this include: (1) Locate the HAS with ultrasound; (2) push the needle directly down toward the HAS; (3) Achieve the proper impedance; (4) Inject the tumescent fluid; (5) Reposition the device down the vein and repeat the process. In some embodiments, aspiration and flashback as well as ultrasound imaging is used to ensure proper location.

In some embodiments, the delivery of the tumescent fluid may be according to the following method: Use a compression means and/or Doppler Ultrasound to identify the location of the target valve; (2) compress the target region and assess whether the reduced diameter does indeed rectify the incompetence; (3) mark the location on the skin; (4) position a needle tip at a location which allows at least two other placements around the HAS at uniform spacing; (5) inject sufficient volume of tumescent fluid to cause the region to slightly tumesce; (6) repeat the steps above in at least two other locations around the HAS.

In some embodiments, HAS therapy may be provided in combination with delivery of tumescent fluid outside the HAS. For example, RF electrode therapy or heating coil therapy can be used.

In some embodiments, tumescent fluid may be delivered by laying a fluid tube with needles connected on the outside of the skin along a vein. The needles could then be pushed toward the skin to penetrate body tissue and inject tumescent fluid.

IV. Tumescent Fluid

Any known type of tumescent fluid can be used in connection with the disclosed apparatus and methods, such as saline or lidocaine with or without epinephrine. The tumescent fluid could also be a solid, gas, cold or chilled fluid, gel, or any other type of fluid. Preferably, the tumescent consists of saline and lidocaine, with or without epinephrine. The fluid primarily acts as an analgesic, but also the nature of the fluid may improve the thermal isolation or facilitate movement of the fluid along the HAS. For example, gas may be a good thermal isolator and may travel easily along the length of the vein. Additionally, the temperature, pressure or volume or other properties of the tumescent fluid can be varied to provide better therapy through tumescent anesthesia. For example, super chilled (or iced) tumescent fluid may provide a better heat sink. Additionally, viscosity additives may alter the heat capacity. In some embodiments, a pump is used to transport the tumescent fluid to the desired location. In some embodiments, a pump is included that cools, mixes and monitors dosage of the tumescent fluid. The pump may be configured with an alarm that factors in the patient's weight. In some embodiments, tumescent fluid is introduced in one location relative to the HAS and then is mechanically pushed along the length of the HAS by massaging the tissue by hand through the patient's skin. In other embodiments, the tumescent fluid is introduced in one location and as the volume is increase the fluid travels along and around the fascial envelop to envelop and compress the HAS.

In addition, one or more bulking agents may be used in connection with the disclosed apparatus and methods. A bulking agent is a relatively inert agent, such as a bioabsorbable gel or liquid, that simply occupies space in or "bulks" the tissue into which the agent is injected.

V. Sterilization

Additional embodiments comprise methods of sterilization. Certain such methods can comprise sterilizing, either terminally or sub-terminally, any of the apparatus disclosed herein that are intended for insertion into (or other contact with) the patient or that are intended for use at or near the surgical field during treatment of a patient. Any suitable method of sterilization, whether presently known or later developed, can be employed.

Accordingly, certain methods comprise sterilizing, either terminally or sub-terminally, any one or combination of the apparatus depicted in FIG. 1, 1A, 1B, 1C, 2, 3, 4, 5, 6, 7, 8, 9, 10, 11, 12, 13, 14, 15, 15A, 16, 16A, 17, 17A, 19, 19A, 19B, or 20. Any suitable method of sterilization, whether presently known or later developed, can be employed. For example, the method can comprise sterilizing any of the above-listed apparatus with an effective dose of a sterilant such as cyclodextrin (Cidex™), ethylene oxide (EtO), steam, hydrogen peroxide vapor, electron beam (E-beam), gamma irradiation, x-rays, or any combination of these sterilants.

The sterilization methods can be performed on the apparatus in question while the apparatus is partially or completely assembled (or partially or completely disassembled); thus, the methods can further comprise partially or completely assembling (or partially or completely disassembling) the apparatus before applying a dose of the selected sterilant(s). The sterilization methods can also optionally comprise applying one or more biological or chemical indicators to the apparatus before exposing the apparatus to the sterilant(s), and assessing mortality or reaction state of the indicator(s) after exposure. As a further option, the sterilization methods can involve monitoring relevant parameters in a sterilization chamber containing the apparatus, such as sterilant concentration, relative humidity, pressure, and/or apparatus temperature.

In view of the foregoing discussion of methods of sterilization, further embodiments comprise sterile apparatus. Sterile apparatus can comprise any of the apparatus disclosed herein that are intended for insertion into (or other contact with) the patient or that are intended for use at or near the surgical field during treatment of a patient. More specifically, any one or combination of the apparatus depicted in FIG. 1, 1A, 1B, 1C, 2, 3, 4, 5, 6, 7, 8, 9, 10, 11, 12, 13, 14, 15, 15A, 16, 16A, 17, 17A, 19, 19A, 19B, or 20 can be provided as a sterile apparatus.

Except as further described herein, the embodiments, features, systems, devices, materials, methods and techniques described herein may, in some embodiments, be similar to any one or more of the embodiments, features, systems, devices, materials, methods and techniques described in U.S. Patent Application Publication No. 2006/0030849A1, published on Feb. 9, 2006, titled METHODS AND APPARATUS FOR COAGULATING AND/OR CONSTRICTING HOLLOW ANATOMICAL STRUCTURES; or in U.S. Patent Application Publication No. 2006/0085054A1, published on Apr. 20, 2006, titled METHODS AND APPARATUS FOR TREATMENT OF HOLLOW ANATOMICAL STRUCTURES; or in U.S. Pat. No. 6,769,433 issued on Aug. 3, 2004 to Zikorus et. al., titled EXPANDABLE VEIN LIGATOR CATHETER HAVING MULTIPLE ELECTRODE LEADS, AND METHOD; or in U.S. Pat. No. 6,752,803 issued on Jun. 22, 2004 to Goldman et al., titled METHOD AND APPARATUS FOR APPLYING ENERGY TO BIOLOGICAL TISSUE INCLUDING THE USE OF TUMESCENT TISSUE COMPRESSION; or in U.S. Provisional Application No. 60/780,948, filed Mar. 9, 2006, entitled SYSTEMS AND METHODS FOR TREATING A HOLLOW ANATOMICAL STRUCTURE. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned U.S. patents, Publications and provisional application. The entirety of each of these patents, publications and provisional application is hereby incorporated by reference herein and made a part of this specification.

A number of applications, publications and external documents are incorporated by reference herein. Any conflict or contradiction between a statement in the bodily text of this specification and a statement in any of the incorporated documents is to be resolved in favor of the statement in the bodily text.

While certain embodiments of the invention(s) have been described, these embodiments have been presented by way of example only, and are not intended to limit the scope of the disclosure. Indeed, the novel methods and systems described herein may be embodied in a variety of other forms; furthermore, various omissions, substitutions and changes in the form of the methods and systems described herein may be made without departing from the scope of the disclosure.

What is claimed is:

1. A method of treating a hollow anatomical structure (HAS) comprising a plurality of quadrants, the method comprising:
   a) positioning a distal end of a probe at a treatment location within the HAS;
   b) delivering RF energy to electrodes disposed at the distal end of the probe such that RF energy is passed through an inner wall of the HAS at the treatment location; and
   c) sequentially treating each quadrant of the plurality of quadrants of the HAS to affect 360 degrees of a diameter of the HAS at the treatment location.

2. The method of claim 1, wherein positioning the distal end of the probe comprises percutaneously introducing the distal end of the probe to the treatment location within the HAS.

3. The method of claim 1, wherein sequentially treating each quadrant of the plurality of quadrants of the HAS comprises providing RF energy for the same amount of time in each quadrant.

4. The method of claim 3, wherein RF energy is provided for one minute in each quadrant of the plurality of quadrants.

5. The method of claim 1, wherein delivering RF energy to the electrodes comprises delivering RF energy to a proximal electrode and to a distal electrode.

6. The method of claim 5, wherein the proximal electrode and the distal electrode are mounted on separate flexible shafts.

7. The method of claim 5, wherein the proximal electrode is the outermost portion of the probe.

8. The method of claim 1, wherein positioning the distal end of the probe at the treatment location within the HAS comprises placing the electrodes in apposition with a wall of the HAS.

9. The method of claim 1, further comprising, following treating each quadrant of the plurality of quadrants of the HAS, moving the probe longitudinally along the HAS and repeating steps a)-c).

10. The method of claim 1, wherein sequentially treating each quadrant of the plurality of quadrants of the HAS comprises sequentially moving the probe 90 degrees to treat each quadrant of the plurality of quadrants.

11. The method of claim 1, wherein the electrodes are single polarity electrodes.

12. The method of claim 1, wherein the HAS comprises a blood vessel.

13. A method of treating a hollow anatomical structure (HAS) comprising a plurality of quadrants, the method comprising:
   a) positioning a distal end of a probe at a treatment location within the HAS;
   b) delivering RF energy from the probe to an inner wall of the HAS at a 0 degree position at the treatment location; and
   c) delivering RF energy from the probe to the inner wall of the HAS at a 90 degree position at the treatment location;
   d) delivering RF energy from the probe to the inner wall of the HAS at a 180 degree position at the treatment location; and
   e) delivering RF energy from the probe to the inner wall of the HAS at a 270 degree position at the treatment location, wherein the RF energy is delivered sequentially at each 90 degree interval to treat each quadrant of the plurality of quadrants.

14. The method of claim 13, wherein positioning the distal end of the probe comprises percutaneously introducing the distal end of the probe to the treatment location within the HAS.

15. The method of claim 13, wherein RF energy is delivered for the same amount of time at each 90 degree interval.

16. The method of claim 13, further comprising, following delivering RF energy to each quadrant of the plurality of quadrants of the HAS, moving the probe longitudinally along the HAS and repeating steps a)-e).

17. The method of claim 13, wherein the HAS comprises a blood vessel.

* * * * *